(12) United States Patent
Sharma et al.

(10) Patent No.: US 12,429,993 B2
(45) Date of Patent: Sep. 30, 2025

(54) SYSTEMS AND METHODS FOR MULTI-BROWSER VIEWERS

(71) Applicant: GE Precision Healthcare LLC, Wauwatosa, WI (US)

(72) Inventors: Ashish Kumar Sharma, Bangalore (IN); Praveenkumar Jeyakumar, Bangalore (IN); Nandan Jain, Bangalore (IN); Pavankumar N R, Bangalore (IN); Vijay Kumar Reddy Arlagadda, Hoffman Estates, IL (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 445 days.

(21) Appl. No.: 17/990,894

(22) Filed: Nov. 21, 2022

(65) Prior Publication Data

US 2024/0168600 A1 May 23, 2024

(51) Int. Cl.
*G06F 3/0481* (2022.01)
*G06F 3/14* (2006.01)
*G16H 10/60* (2018.01)

(52) U.S. Cl.
CPC .......... *G06F 3/0481* (2013.01); *G06F 3/1423* (2013.01); *G16H 10/60* (2018.01); *G06F 2203/04803* (2013.01)

(58) Field of Classification Search
CPC .. G06F 3/0481; G06F 3/04845; G06F 3/1423; G06F 2203/04803; G16H 10/60
See application file for complete search history.

(56) References Cited

U.S. PATENT DOCUMENTS

| | | | |
|---|---|---|---|
| 5,821,927 A * | 10/1998 | Gong | G06F 3/0481 715/822 |
| 7,581,186 B2 * | 8/2009 | Dowdy | G06F 16/68 715/727 |
| 7,836,303 B2 | 11/2010 | Levy | |
| 8,036,917 B2 | 10/2011 | Kariathungal | |
| 8,250,653 B2 | 8/2012 | Wang | |
| 8,341,268 B2 | 12/2012 | Wang | |
| 8,526,693 B2 | 9/2013 | Vijaykalyan | |
| 9,152,760 B2 * | 10/2015 | Sherman | G16H 30/20 |
| 9,413,807 B1 | 8/2016 | Sherman | |
| 11,328,381 B2 | 5/2022 | Westerhoff | |
| 2007/0245260 A1 * | 10/2007 | Koppert | G06F 16/34 715/810 |
| 2009/0249216 A1 * | 10/2009 | Charka | G06F 11/3688 715/744 |

(Continued)

FOREIGN PATENT DOCUMENTS

| | | |
|---|---|---|
| CN | 108762868 B | 7/2022 |
| EP | 2735982 A1 | 5/2014 |

*Primary Examiner* — Ting Z Lee

(57) ABSTRACT

Systems and methods for multi-browser viewers are proposed. A multi-browser system may include multiple browsers as hanging windows in a computer display system. Each browser is its own computer process for individual process management in memory and recovery if the process runs into issues. The system and methods proposed herein allow for the multiple browsers to be coordinated as to the information and views they are sharing to help users understand multiple sources of information quickly and in connection with each other. Such a system may be applicable in the healthcare industry, as one example.

19 Claims, 17 Drawing Sheets

(56) References Cited

U.S. PATENT DOCUMENTS

| | | | |
|---|---|---|---|
| 2014/0028784 A1* | 1/2014 | Deyerle | H04L 65/403 |
| | | | 348/E7.083 |
| 2014/0140589 A1 | 5/2014 | Klotzer | |
| 2014/0143271 A1 | 5/2014 | Klotzer | |
| 2014/0143298 A1 | 5/2014 | Klotzer | |
| 2015/0007015 A1* | 1/2015 | Nekkalapudi | G06F 16/954 |
| | | | 715/234 |
| 2017/0039348 A1* | 2/2017 | Fram | G06F 40/166 |
| 2017/0262960 A1* | 9/2017 | Cheng | G06T 11/60 |
| 2024/0220343 A1* | 7/2024 | Rao | G06F 16/9577 |

\* cited by examiner

SYSTEMS AND METHODS FOR MULTI-BROWSER VIEWERS

TECHNICAL FIELD

The subject matter disclosed herein relates generally to technology for visualization of, and interaction with, digital content on display screens using computer technology.

BACKGROUND

Digital computer technologies are used often to convey multiple types of information to users. Hardware and software interact to provide information and visual output analysis to users. Such computer technologies that can present relevant, helpful information to users for decision making are valuable.

One type of user is that of a healthcare worker who is seeking to learn more about a patient, patient condition, or medical issue. The healthcare worker may need to make decisions related to human life based on information stored in computer technologies. Multiple forms of information may be needed, such as electronic medical record (EMR) data, radiology reports, medical images of various modalities and views, previous histories, and the like. These are hard to show well simultaneously for users to make smart decisions. Systems and methods for an improved viewing and coordinated viewing experiences are herein proposed.

Further, having so much information to show to a user can place a large burden on the computer processor, memory, and software operating system. Single browser and single process systems can be slow and burdensome, providing an unsatisfactory experience that can cost healthcare providers time and money. Systems and methods for improved multi-browser viewers are herein proposed.

BRIEF DESCRIPTION

In accordance with an aspect, a system is provided that can include a processor for executing a plurality of computer processes; a memory that stores digital content for use by said computer processes during execution by the processor; a monitor for displaying a user interface; a first browser process executed by the processor that accesses digital content from the memory, wherein the first browser displays digital content in a user interface window on the monitor; a second browser process executed by the processor that accesses digital content from the memory, wherein the second browser displays digital content in a user interface window on the monitor simultaneously to the first browser process; and wherein the user interface windows for each process are displayed in a hanging layout on the monitor. The first browser process and the second browser process may be displayed on the monitor in headless user interface windows.

The system can further include an input device for a user to interact the user interface; a coordination browser process executed by the processor that provides coordination between the first browser process and second browser process; and wherein the coordination browser allows the input device to manipulate digital content simultaneously in both the first and second browser. Further, the digital content displayed in both the first browser and second browser is medical digital content; the medical digital content displayed in both the first browser and the second browser is not the same digital content; and the medical digital content in both browsers is related to the same patient. The coordination browser may use at least one message channel process to facilitate cross-browser coordination. The digital content can be a cine.

The system can further include a second monitor for displaying the user interface; a third browser process executed by the processor that accesses digital content from the memory, wherein the third browser displays digital content in a user interface window on the second monitor; a common message channel for cross browser communication between at least two of the processes; and wherein at least two of the browser processes coordinate their displayed digital content through the common message channel. The common message channel can be implemented as an application programming interface (API).

The system can further include a controller browser process executed by the processor that allows a user to access control functions related to at least one of browser processes, wherein the controller browser displays control functions in a user interface window on the monitor; and each control function allows a user to interact with the digital content in at least one of the first browser process or the second browser process. The system can also perform the steps of detecting the user interface usage patterns of at least one user; and running an artificial intelligence algorithm based on the usage patterns to either provide automated user interface windows to the user or allocate memory and system resources.

The system may also detect its health and fix issues. The first browser process and second browser process can detect the digital health of its respective process, and provide an indication on the user interface related to the digital health of its process. The user interface can accept a user command to restart at least one of the first browser process or second browser process. The digital health of a computer process can be related to its interaction with the memory. Further, each of the first browser process and second browser process can detect its respective digital health, related to its interactions with the processor and memory; and if the digital health is detected as not healthy, each browser process can restart itself. Each browser process has a separate allocation of memory. Further, as the processor allocates digital content to each browser process, the size of the digital content is considered compared to the separate allocation of memory for the related browser process.

In accordance with an aspect, a computer-implemented method is proposed, including displaying a user interface on a monitor; loading multiple browser windows with digital content, wherein each browser is run as a separate computer process and has a separate memory allocation than the other browsers, and wherein the memory allocation for each browser is based on the size of the digital content to be displayed by that browser; displaying the multiple browser windows within the user interface; providing coordination between browsers through digital communication channels; and allowing for user interaction with the browser windows.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description.

BRIEF DESCRIPTION OF THE DRAWINGS

Numerous aspects, implementations, objects and advantages of the present invention will be apparent upon consideration of the following detailed description, taken in conjunction with the accompanying drawings, in which like reference characters refer to like parts throughout, and in which.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized, and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

There is a need to improve performance of medical image viewers and cine viewers as all the displaying and viewing happens into a single browser with split screens within it. All the screens share the same memory of the browser. The embodiments herein propose an improved technical effect of a screen layout where each split screen is an individual headless browser windows which have their own allocated memory and each browser window is used for different functionality (cine, different views if an anatomy etc.) giving a very smooth computer processing & memory efficient viewing performance. There are benefits in embodiments herein when implementing a view system that requires a lot of memory such as cardiology use-cases where full fidelity cine is hard to achieve.

Figure 1:
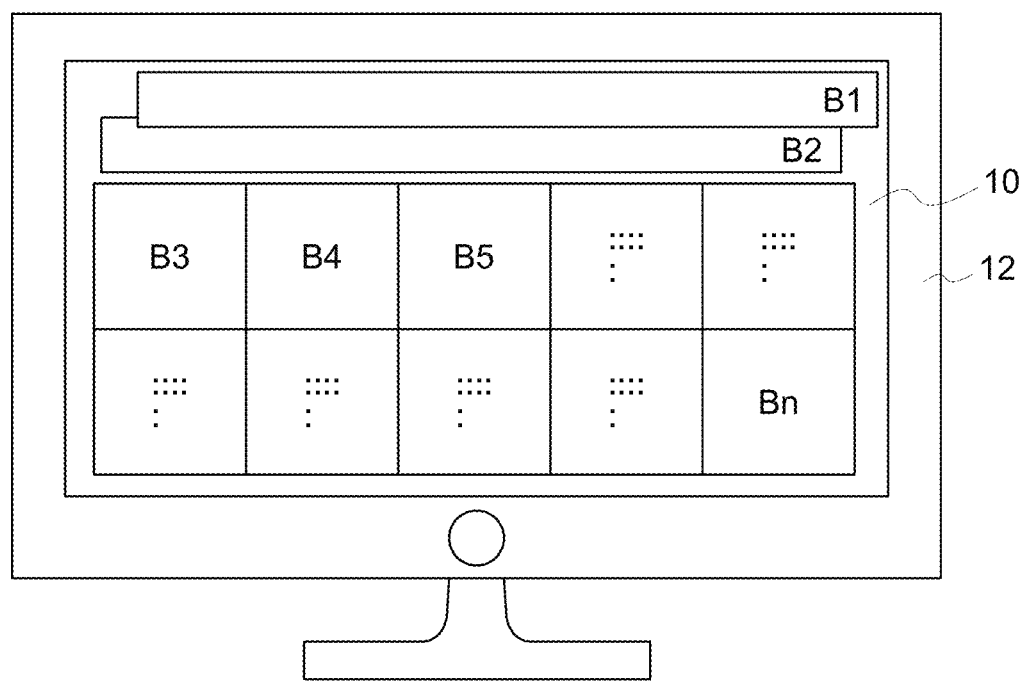
FIG. 1 shows a multi-browser system, according to an embodiment.

FIG. 1 shows a multi-browser system, according to an embodiment. FIG. 1 includes computer monitor 12, user interface 10, browser controller B1, browser navigator B2, and browsers B3, B4, B5 . . . Bn. A browser is a computer process that provides a visual display such that the user can browse information and interact with the computer in various ways. For example, in a healthcare setting, browsers can represent an image layout, medical study, a group, a report, or information navigator. Such information may be provided from a hard drive, computer network, local memory, remote memory, an edge device, the internet, or other locations.

Figure 2:
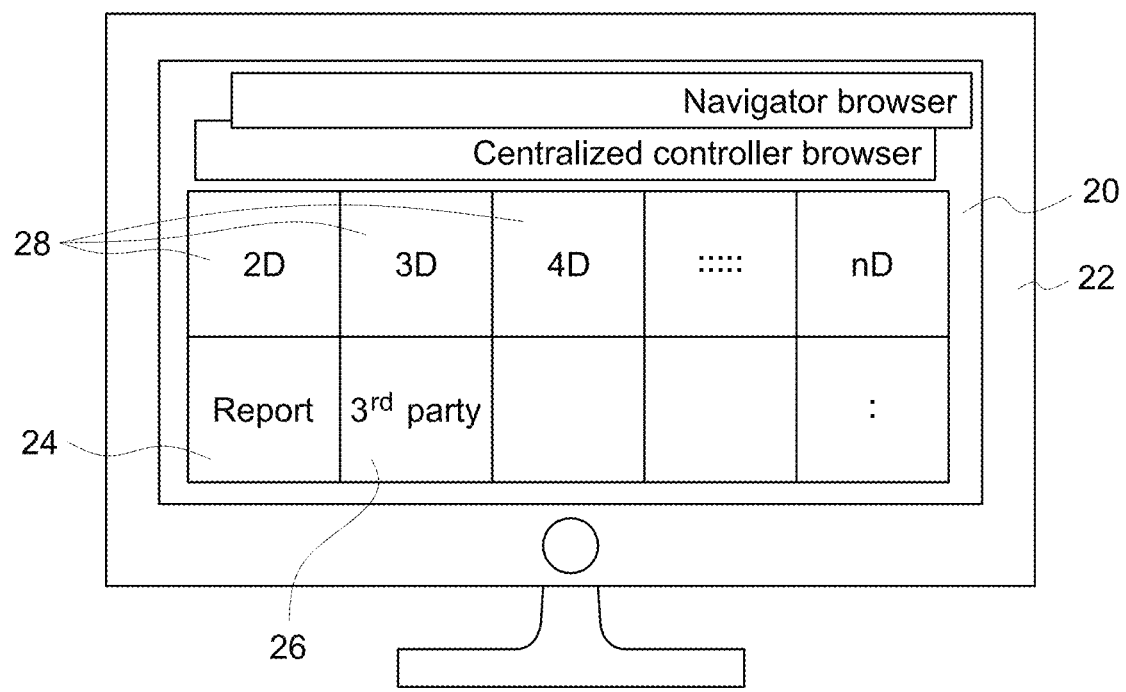
FIG. 2 shows a multiple use multi-browser system, according to an embodiment.
Figure 3:
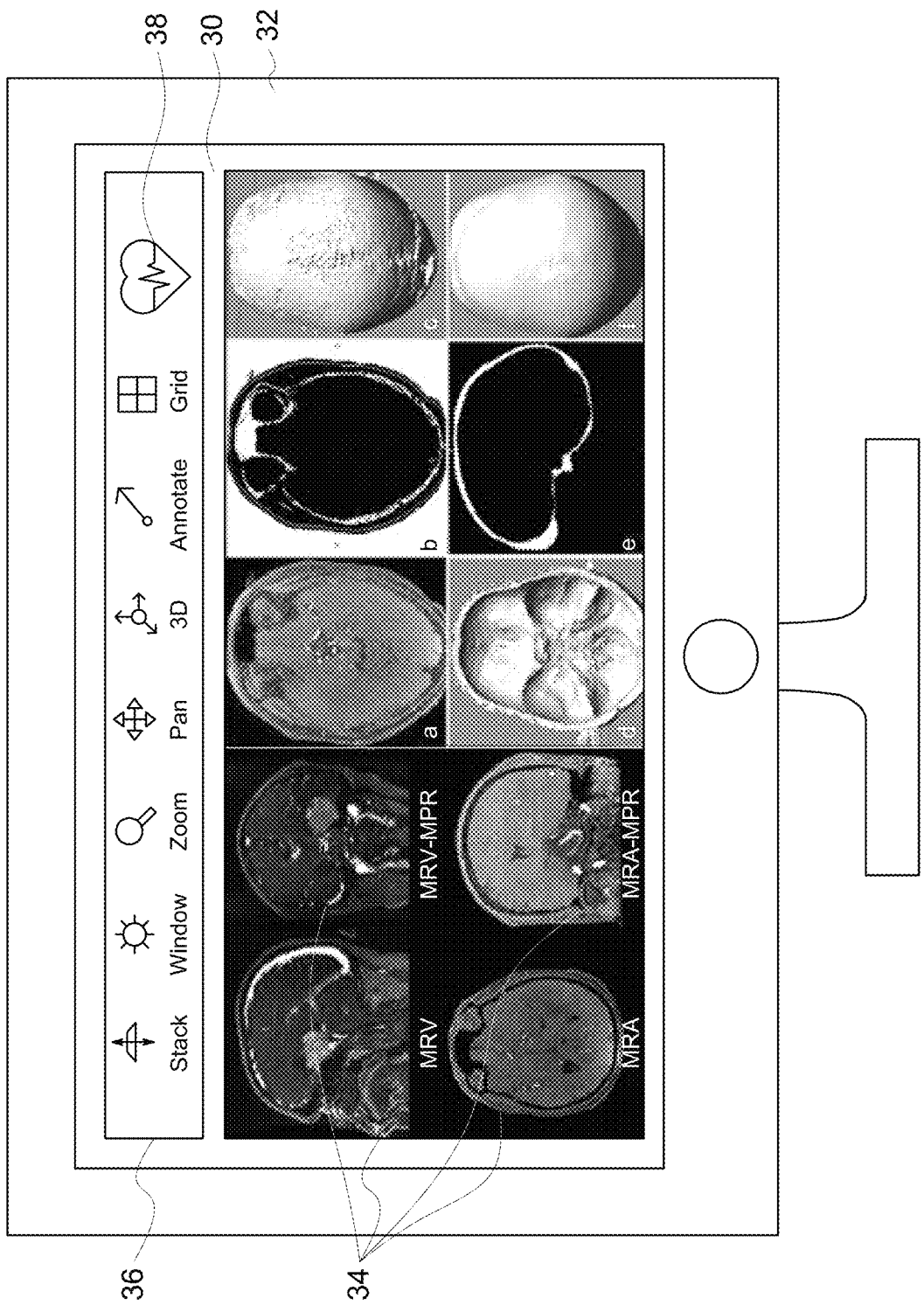
FIG. 3 shows a medical multi-browser system, according to an embodiment.
Figure 4:
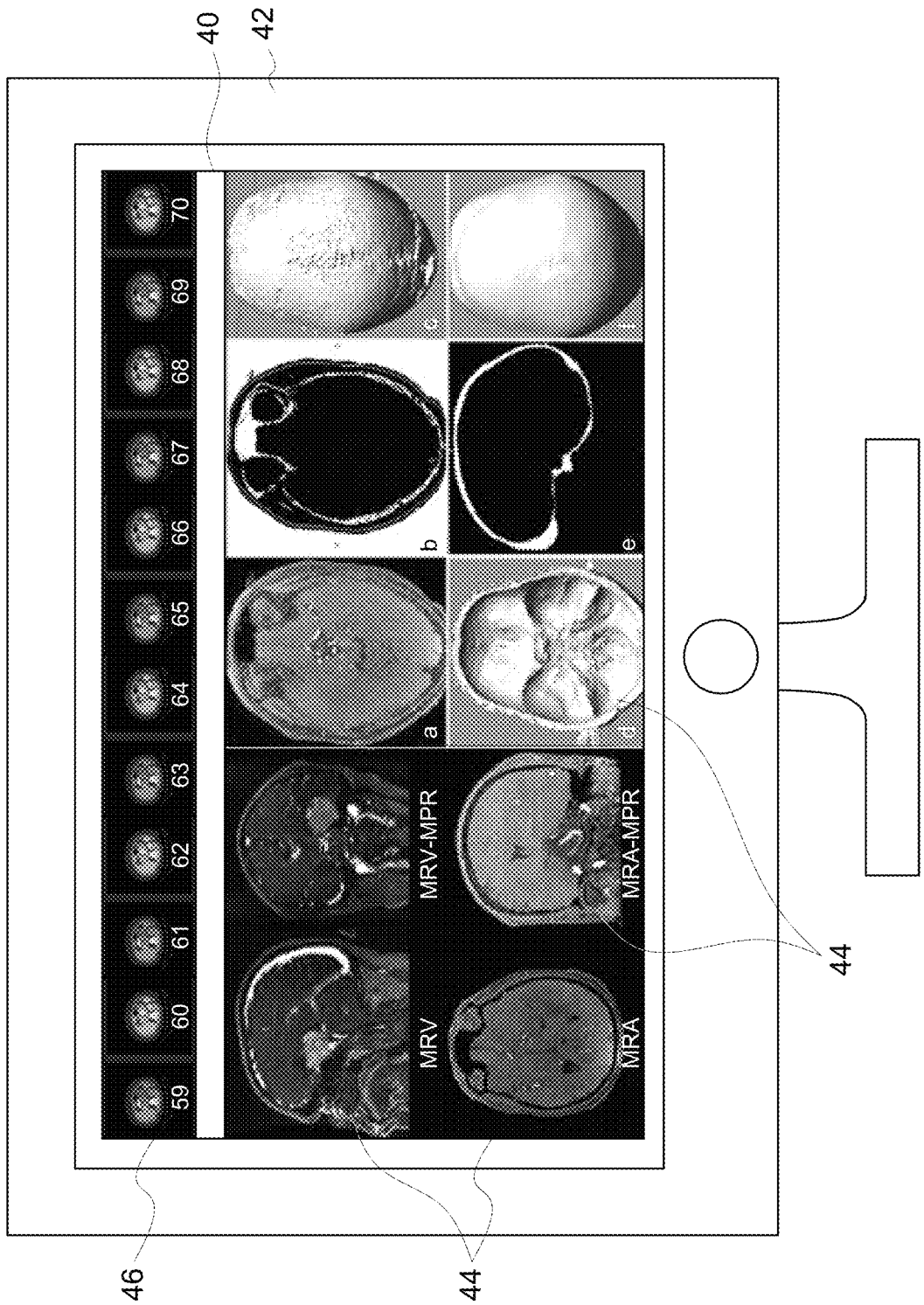
FIG. 4 shows a medical series multi-browser system, according to an embodiment.

User interface 10 may be a smart viewer, which leverages multiple browsers to display related information in the browser to help users make decisions and interact with computer content. Thus, each browser in a smart viewer may have information components that are in similar categories or related to similar events. In one embodiment, this may be medical information related to a specific patient or medical condition, such as shown in FIGS. 2-4.

In another embodiment the smart viewer may show differing data from a sports event for a coach to process the information about a play. The browsers may show different video views of a play, numbered data about the event, statistics about the event compared to past events, artificial intelligence suggestions about how the play may be executed better in the next game, controls to swap out players and circumstances, and similar types of sports analysis.

In another embodiment the smart viewer may show police differing data from a crime scene. The browsers may show different surveillance footage views of a location, timing information about interactions about the event, information from databases about the people in the views or related to the event, emergency call information, historical information about the location, police investigator analysis, and similar types of police analysis. It may thus be seen that such a smart viewer with multiple browsers, which may be coordinated, can apply across many types of technology, government, healthcare, education, and media industries.

Browsers B1-Bn are shown as headless browsers, meaning they do not have a header along the top of their browser window. In FIG. 1, each browser B1-Bn is organized in tabular format to form a hanging protocol. FIG. 1 shows a hanging layout with multiple browsers. Each browser may run a separate feature specific algorithm or process. Thus, "n" number of browsers can run "n" number of feature specific algorithms. Each browser may be contained as its own process, and thus the reloading of browsers that are malfunctioning or having issues does not cause interruptions or disruptions on other browsers in the system. This has the technical effect of improving performance in the smart viewer and overcomes limitations of previous browser-based applications.

FIG. 2 shows a multiple use multi-browser system, according to an embodiment. FIG. 2 includes operator console 22, multi-browser user interface 20, image data browsers 28, written report browser 24, and third ($3^{rd}$) party browser 26.

In one embodiment multi-browser user interface 20 is a medical smart viewer software and hardware system. Thus, the image views of image data browsers 28 may be two-dimensional (2D), three-dimensional (3D), and four-dimensional (4D) DICOM medical image data. DICOM®—Digital Imaging and Communications in Medicine—is an international standard for medical images and related information. It defines the formats for medical images that can be exchanged with the data and quality necessary for clinical use. Other image data formats may be used in other embodiments. Related reports in written report browser may be radiology report, medical appointment reports, office notes, or other written information in an embodiment. Thus, the multi-browser user interface 20 may be a smart DICOM viewer that utilizes multiple browsers to hang different components of medical information separately. The navigator browser may be used to see thumbnails of all series/groups of a patient history report, as will be further discussed herein.

Each browser runs a separate computer software process with the computer processing unit and is isolated in memory allocation from other browsers. Thus, each browser acts as an independent cell, with all of its complete functionality therein. While the browsers may be coordinated as discussed further herein, they all may be independent in functionality and computer process allocation. This allows for a larger number of exams, images, applications, processed, reports, and more to be displayed and interacted with for users.

FIG. 3 shows a medical multi-browser system, according to an embodiment. FIG. 3 includes operator console with monitor 32, medical user interface 30, headless browsers 34, controller browser 36, and browser health check icon 38. A clinician, physician, doctor, nurse, or other healthcare worker may use such a medical user interface 30 for analyzing medical information for diagnosis and medical decision making.

Headless browsers 34 are all separate browser windows that are being run as separate processors in the memory and central processing unit(s). These are run all as part of medical user interface 30 application, not as separate applications, according to an embodiment. Headless browsers 34 show different cranial views of a patient. Some views are 2D, some views are 3D, some have contrast, others are from different angles. As one aspect, the various headless browsers show separate features of the same study or image. One browser can display 2D images, one can display 3D images, another bowser can display AI finding on the same study, and another browser can display images in different views (angles, contrast inverted). Headless browsers can also be used for displaying studies with different feature functionalities. The system can also integrate with third party software applications that may be related to the other browsers or decision to be made.

Controller browser 36 is a headless browser window similar to headless browsers 34, except its process has control information related to the headless browsers 34. Control functions for interaction by a user are presented in controller browser 36. Examples according to one embodiment include stacking headless browsers, window brightness levels, zooming into the detail of the content a headless browser, panning around the content in a headless browser, changing 3D ratios and rotations within headless browser views, annotating information within a specific headless browser, and re-establishing how the grid of headless browsers should be displayed. Controller browser 36 acts as a manager and includes viewer specific tools.

Browser health check icon 38 is also included in this embodiment of controller browser 36. Since each headless browser 34 is its own computer process, each process may have its own status and may run into its own separate issues. These may be buffer overflows, lagging communications, memory corruption, browser memory issues, browser crashes, and other computer issues affecting processes. This tracks the health of headless browsers 34. Browser health check icon 38 can be interacted with, for example clicking on, and then provides further information about the status of headless browsers 34. Further, interacting with browser health check icon 38 may reveal sub menus for restarting processes, different visual options, and browser process diagnostics. This is discussed further in relation to additional figures and embodiments.

FIG. 4 shows a medical series multi-browser system, according to an embodiment. FIG. 4 includes computer hardware monitor 42 with display screen showing medical user interface 40, medical image browsers 44, and browser coordinator 46. A radiologist, for example, may look at image scans from a variety of modalities to compare image results. These modalities may be computed tomography (CT), magnetic resonance imaging (MRI), X-ray, positron emission tomography (PET), ultrasound, single-photon emission computerized tomography (SPECT), or other forms of medical image acquisition.

FIG. 4 shows how, while medical image browsers 44, are separate processes, there can be cross-process/cross-browser coordination. In an example embodiment, browser coordinator 46 shows the image thumbnails of a series of images in a medical image study or examination. Each thumbnail is at a different time, angle, or region of interest (ROI) location. As a user slides their input device, such as a mouse or a finger, across the screen, all of the headless browsers adjust—are coordinated—to show the version of their medical image data taken from the exact same time, angle, or ROI. Thus, a 3D image can be adjusted simultaneously as a 2D and 4D image related to the same angle of viewing as is selected in browser coordinator 46. And changes in time can be seen as the user changes the browser coordinator 46 location of input. In addition to a series, browser coordinator 46 can represent thumbnails of different studies, including prior studies. Another use of browser coordinator 46 may be to show the health status of all the browsers. Another use of browser coordinator 46 may be to show third party application icons that could open in another browser.

FIG. 4 also shows how the smart viewer system and methods herein can show cinematographic (cine) viewing more possible with better memory management and cross-browser coordination. Cine is a feature, using which, radiologists and healthcare workers can see thousands of images in running video mode. This allows the healthcare workers to see all the images in sequence in a running picture mode—either by scrolling in a global stack mode or without further interaction. Thus, this is a visual running of all images, a playing mode over time, in some way similar to a movie playing out across multiple medical headless browsers 44. In previous technologies, cine viewing would overload the memory as one process would be trying to show many views at the same time. By breaking each view into its own browser, better processor and memory management is achieved and more smooth cine viewing can occur for the users. Running cine with large number of images can be solved by using multiple browsers and loading each browsers data separately. The system can pre-load images in new window of medical image browsers 44 instead of purging/loading resized images in same viewport. This extends browser based application to overcome the problems faced by browser based applications due to memory constraints on single browser window and supports multiple hanging protocols.

In some embodiments user interface 40 may show artificial intelligence (AI) findings as alerts, badges, statistics, and other helpful information for a healthcare worker to know about. AI through neural networks or machine learning can also provide a suggested spot along browser coordinator 46 or within a cine that a user may find the most helpful information within headless browsers 44.

Figure 5A:
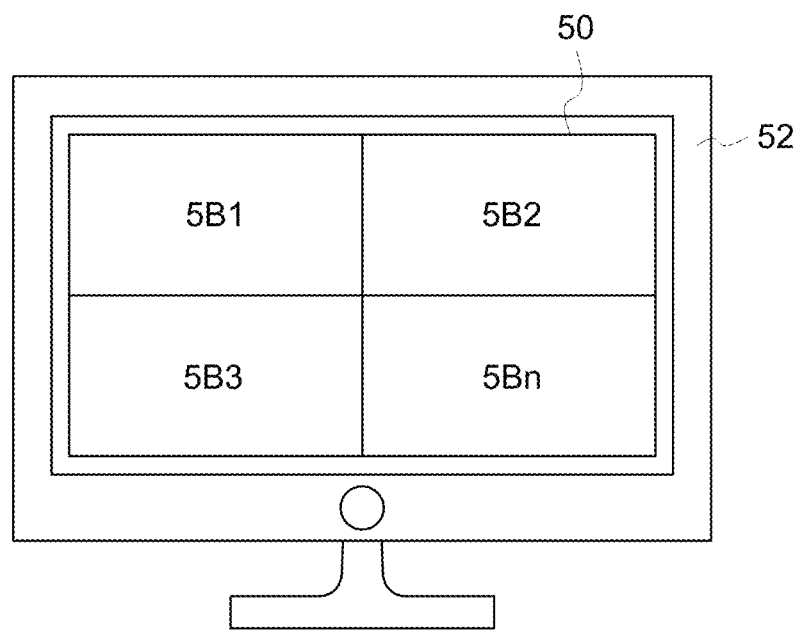
FIG. 5A shows a tree level multi-browser system, according to an embodiment.
Figure 5B:
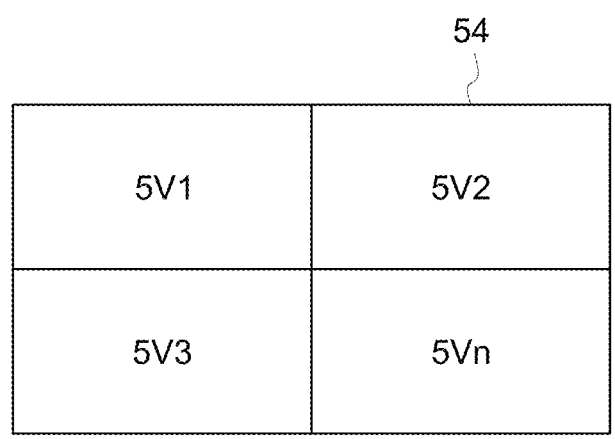
FIG. 5B shows a sub-tree in a multi-browser system, according to an embodiment.

FIG. 5A shows a tree level multi-browser system, according to an embodiment. FIG. 5A includes physical computer display 52 and multi-browser user interface 50. FIG. 5B shows a sub-tree in a multi-browser system, according to an embodiment. FIG. 5B includes a sub-tree user interface 54 in a multi-browser system. Browsers 5B1, 5B2, 5B3 and 5Bn show top level information, such as shown in previous figures. Sub-tree user interface 54 shows a next level down view of 5Bn browser from FIG. 5A.

In an example embodiment, browser 5Bn is a separate process running in the computing system and displaying a medical image. When interacted with, browser 5Bn may expand such that the process shows related images 5V1, 5V2, 5V3, and 5Vn. This sub-tree may be within the smaller section of the screen as shown as 5Bn in FIG. 5B (zoom-in mode)—or can fill up the screen (replacement mode), depending on configuration. Thus, individual groups of images in a browser can be extended into multiple dynamic layouts. Creating multiple viewing regions within a monitor is an improvement over the prior art and a technical effect of embodiments herein. Another example embodiment may have browser 5Bn showing EMR data about a patient. A physician may want more than just a high level summary and interacts with browser 5Bn. As a result, 5V1 shows recent appointment information, 5V2 shows medical history information, 5V3 shows prescription information, and 5Vn shows a recent radiology report. Thus, each browser can provide more detailed views and information when interacted with, making the system dynamic, flexible, and more useful.

Figure 6A:
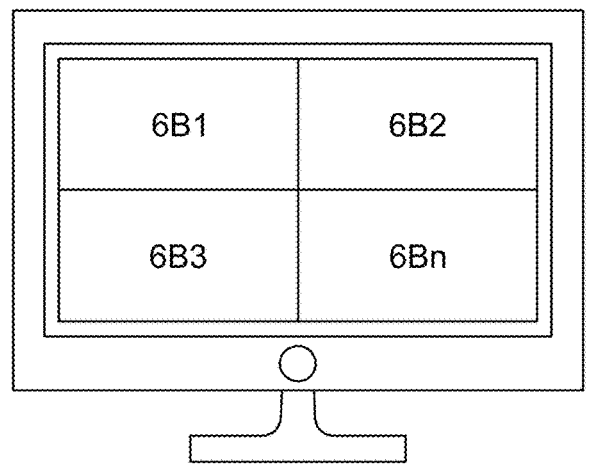
FIG. 6A shows a full view mode navigation multi-browser system, according to an embodiment.
Figure 6B:
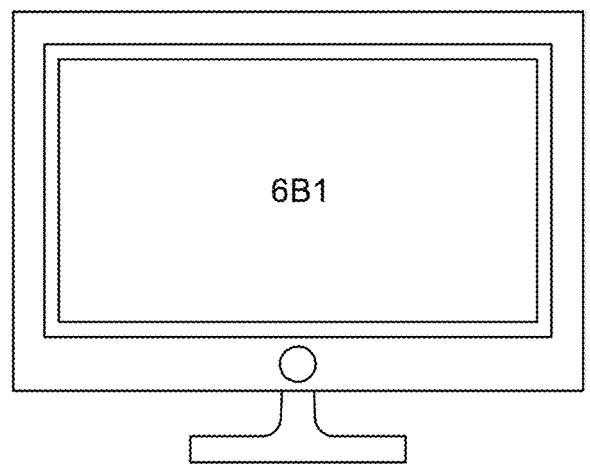
FIG. 6B shows a full view mode of a multi-browser system, according to an embodiment.
Figure 6C:
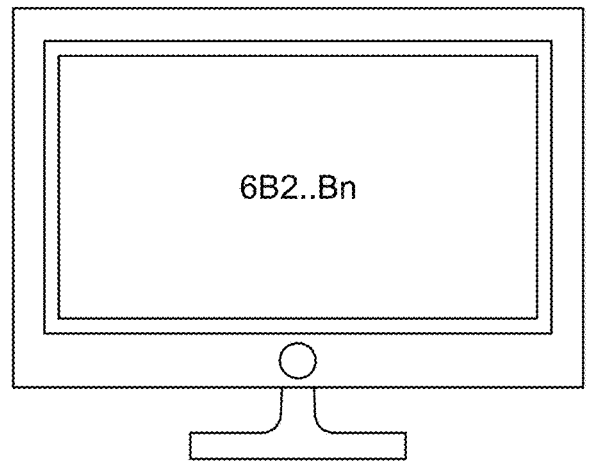
FIG. 6C shows the continued navigation of a full view mode navigation of a multi-browser system, according to an embodiment.

FIG. 6A shows a full view mode navigation multi-browser system, according to an embodiment. FIG. 6B shows a full view mode of a multi-browser system, according to an embodiment. FIG. 6C shows the continued navigation of a full view mode navigation of a multi-browser system, according to an embodiment.

FIG. 6A includes the standard multi-browser system as is discussed in regard to FIG. 2. Browsers 6B1, 6B2, 6B3, and 6Bn (n meaning there can be any number of browsers and four is only an example for illustrative purposes) are individual processes displaying data and/or interactive content for users. If a user chooses to maximize 6B1 they may do so as shown in FIG. 6B. The user may do this with keyboard, touch, mouse, or other ways of inputting commands. Maximizing a window may also be referred to as zooming in to the content within the browser. This is a full view mode for one browser 6B1 to fill the screen of the monitor or display. Then, when in full view mode of FIG. 6B, a user can navigate to the next browser or group of images such as 6B2 or 6Bn as shown in FIG. 6C. This can be achieved by inputs such as a scroll wheel, right and left arrow keys, touch swiping or other types of scroll input. This allows the user to have larger views of individual browsers.

Figure 7A:
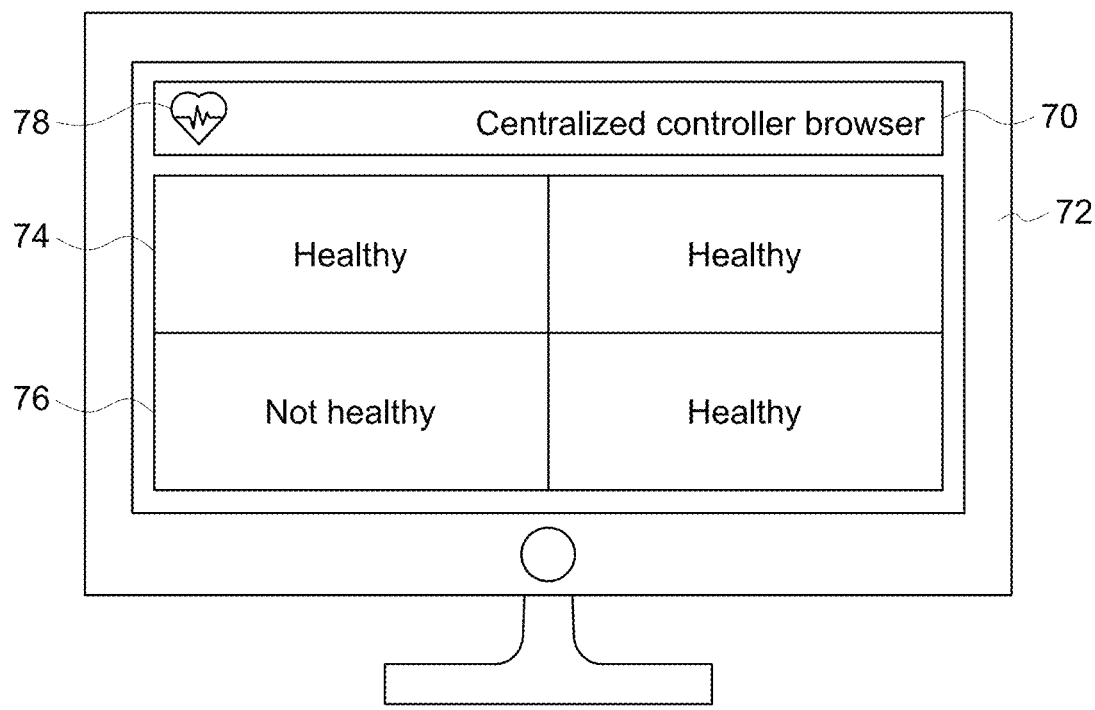
FIG. 7A shows health check feature of a multi-browser system, according to an embodiment.
Figure 7B:
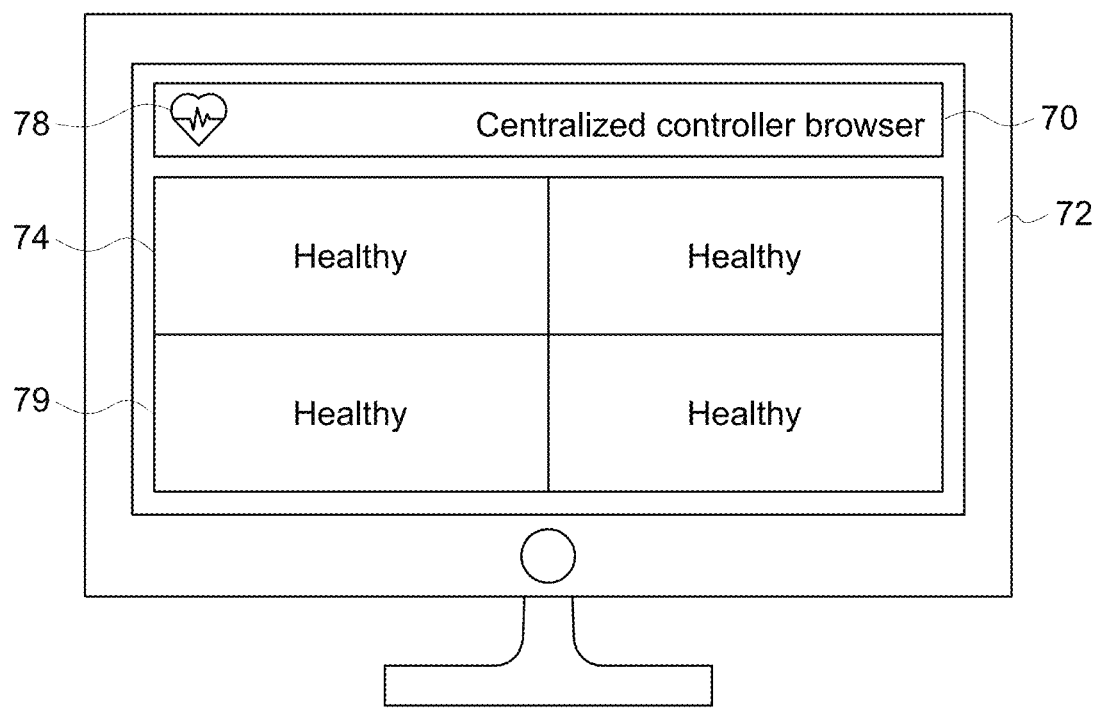
FIG. 7B shows an updated health check feature of a multi-browser system, according to an embodiment.

FIG. 7A shows health check feature of a multi-browser system, according to an embodiment. FIG. 7B shows an updated health check feature of a multi-browser system, according to an embodiment. FIGS. 7A and 7B includes computer display 72 that is displaying a user interface with headless browsers each running as separate computer processes with separate memory allocations. Controller browser 70 provides various controls and interactive options to a user of the system. One such option is the health check option activated by health check icon 78. A user has interacted with health check icon 78 and the headless browsers have shown their health status. Headless browser 74 shows as a healthy computer process state. This may mean that the process is running at full speed in the CPU and has no corrupt memory segments, or delayed memory access. If there are such issues, the headless browser may show an unhealthy notification, as shown in not healthy headless browser 76. Other unhealthy statuses may include the computer memory is low, browser memory is near to the allocated limitation, the slow processing of images, or an inability to contact another browser through the designated message channel, as non-limiting examples. Such notifications may be overlays, may be colored badges, may be percentage healthy indicator, may be a replaced window with only the health status, or other user interface mechanisms for communicating the health of the browser. The smart viewer can also show utilized vs. available memory metrics for each browser. The browser may restart or perform maintenance operations to go from a not healthy headless browser 76 to a healthy browser 79. This may be at the user control or request, or may be automatic based on health status algorithms. The process may restart fully from a default state or may be restarted at the last successful state the browser process was at before it encountered problems.

Because each browser has its own memory allocation, the browsers can render large image or data files with high performance. This includes such content as video files, 3D images, and large series of images. Based on the browser's assigned memory & available RAM "n" browsers can provide "n" GB/MB (gigabyte/megabyte) of memory space to application. Modern operating systems may have memory constraints of four GB per process, so separating the content across different processors allows for less issues of overloading the memory. This allows for a smoother display of images. For example, if there are 10 GB of images, instead of one browser loading all 10 GB and potentially running into performance issues, ten separate browsers may be generated with 1 GB of images loaded into each.

Autocorrection of the smart viewer can occur in an embodiment as shown in FIG. 7A and FIG. 7B. If the system has "n" number of browsers, and one browser is not working or crashed, another browser can spawn and replace the error prone one and avoiding application close or crash. As shown in FIG. 7B, when a browser is in un-responsive mode, browser health check controller can replace a new browser with the last successful state. If the browser memory is low, the system can launch another browser to launch different images instead of restricting the display.

Figure 8:
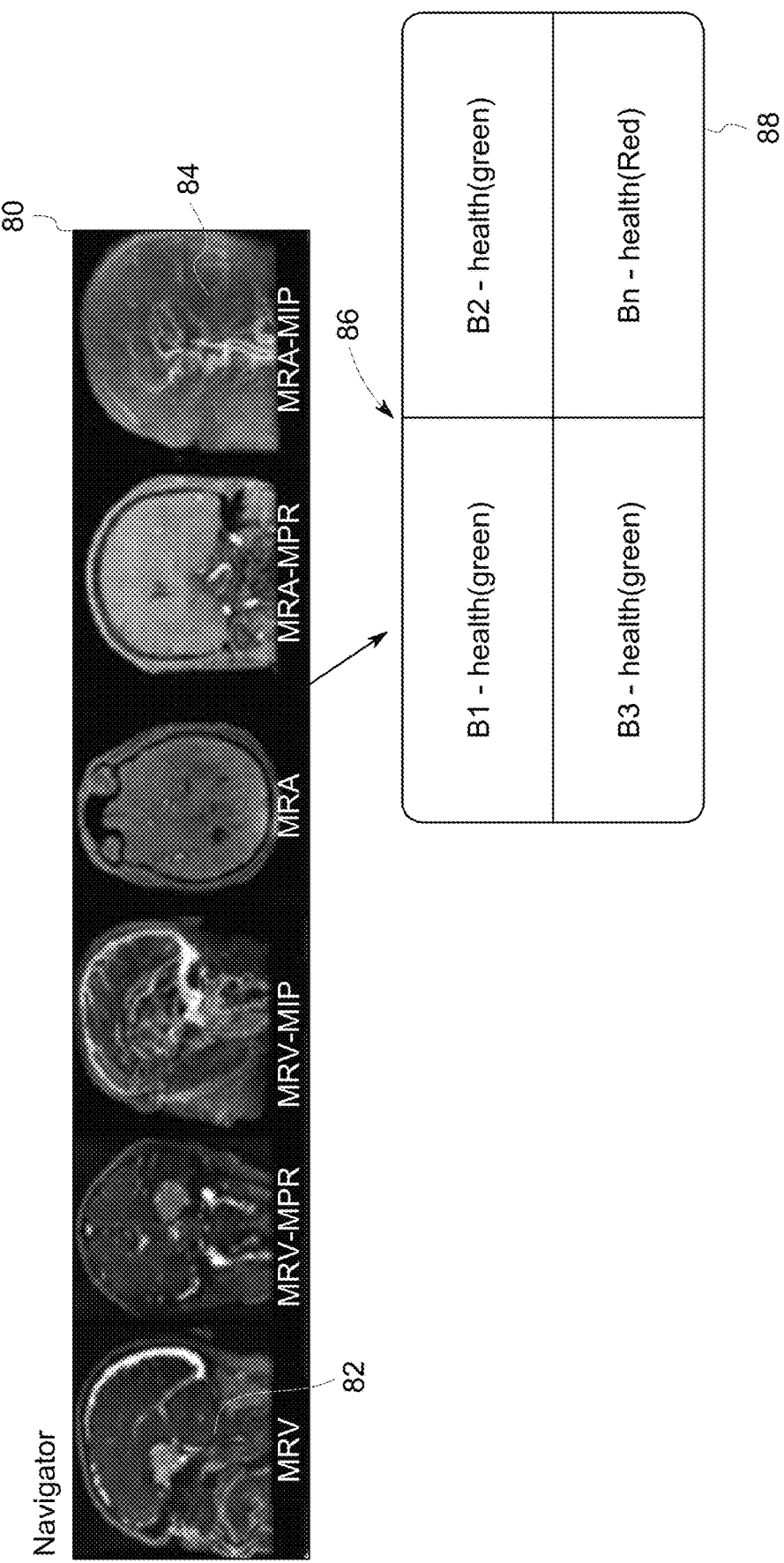
FIG. 8 shows a snap tool approach for a multi-browser system, according to an embodiment.

FIG. 8 shows a snap tool approach for a multi-browser system, according to an embodiment. FIG. 8 includes navigator browser 80, left thumbnail icon 82, right thumbnail icon 84, snap tool 86, and unhealthy indicator 88. Navigator browser 80 shows thumbnails of the various multiple browsers running in the smart viewer. For example, left thumbnail icon 82 may indicate that one browser is currently showing show a left cranial view titled MRV. Right thumbnail icon 84 may indicate a different modality image view titled MRA-MIP, according to this non-limiting example for understanding purposes. On moving mouse in navigator browser 80 which is acting as a thumbnail controller, snap tool 86 presents the health check of each layout browser. In an embodiment, snap tool 86 can show color indications for identifying the health of various browsers. For example, green may indicate that images may be shown with full resolution and speed. Red may indicate that images may not be shown with full resolution or full speed as there is some issue with the process or memory allocation. Interacting further with unhealthy indicator 88 may provide more detailed information related to the issue and options for resolving the issue. Snap tool can also provide a snapshot of all the browsers, where user can navigate the selected thumbnail (representing the series, study) to any of the browser. In an embodiment, by using a snap tool, user can drag the selected thumbnail to a browser location, without moving a mouse to a physical location of the browser. Browser can be in anywhere in the multimonitor scenario also. When the mouse, finger, or other user input hovers over B1, B2, B3, Bn, the system can provide a snapshot of the expanded information for that browser.

Figure 9:
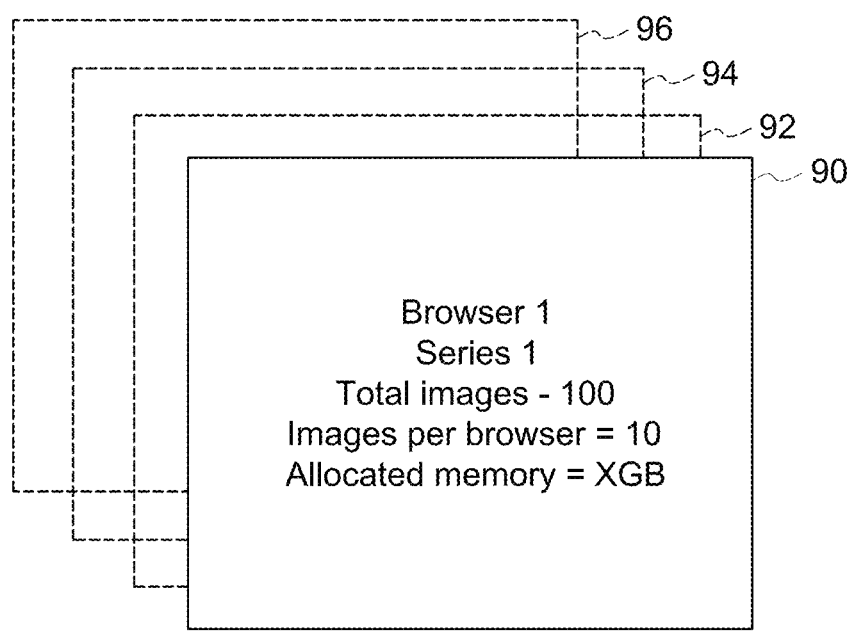
FIG. 9 shows enhanced memory usage for a multi-browser system, according to an embodiment.

FIG. 9 shows enhanced memory usage for a multi-browser system, according to an embodiment. FIG. 9 includes memory allocation information for browser 90, browser 92, browser 94, and browser 96. The system and methods herein are designed to best use the available memory and processing power of a system. The system and methods leverage existing memory of multiple browsers for a single application. The systems and methods use multiple browsers for hanging definition and utilizing browser's memory access. The system and methods herein utilize memory and processing power of hardware to its max by creating more browser processes for loading images.

Each browser has a limited maximum memory based on the operating system or cloud environment. Thus, it is important to utilize multi-browser memory space. For a multi-window hanging browser view, multiple browsers are used. Each content type (image series in a medical example) can be loaded in one browser to display. Each browser instance starts with a maximum allocated memory limit that becomes a memory limitation for the application. Loading the application in multiple browser instances extends the available memory to the application by "n" factor, i.e., total available memory for application=n times×GB. "n" may be determined, in one exemplary embodiment, by calculating size of the number of images equivalent to the browser's allocated memory.

In the system, "n" browsers can be used to run cine with a total capacity of 'n' browsers allocated memory. This method is useful in efficient display of cine without need to flush/load new images in the same browser memory. As shown in FIG. 9, the browsers are loaded and displayed as a stack with only one active browser visible to user, according to an embodiment. On reaching the last image in browser 90, the smart viewer application immediately hides browser 90 and switches control over to browser 92 for uninterrupted continuous display of a cine. The same approach may be used for manual scrolling of images by the user.

Figure 10A:
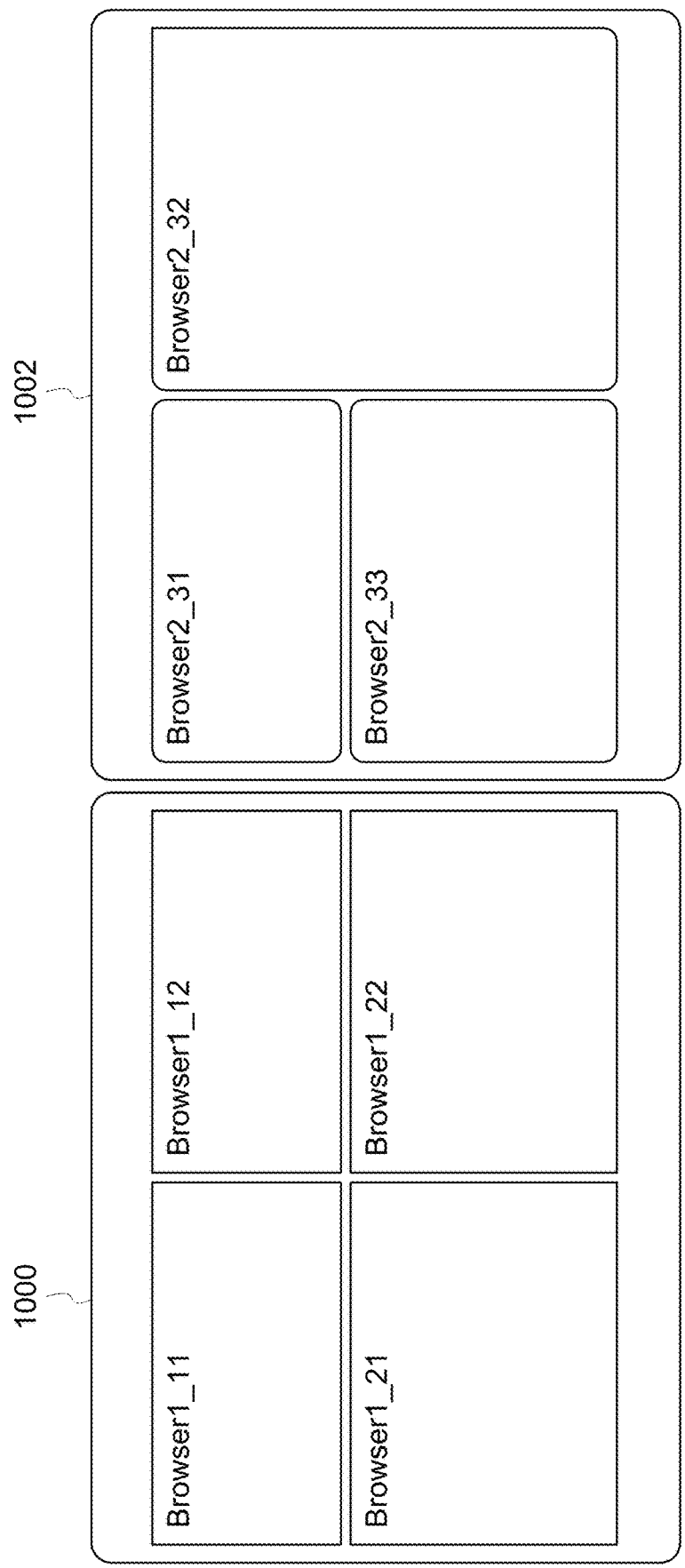
FIG. 10A shows a multi-browser system with multiple monitors, according to an embodiment.

FIG. 10A shows a multi-browser system with multiple monitors, according to an embodiment. FIG. 10A includes a first computer monitor 1000 and a second computer monitor 1002. These may be any type of monitor, including handheld computer displays, tablet computer displays, desktop computer displays, virtual reality displays, augmented reality displays, or laptop computer displays, as non-limiting examples. First computer monitor 1000 includes Browser 1_11, Browser 1_12, Browser 1_21, and Browser 1_22. Second computer monitor 1002 includes Browser 2_31, Browser 2_32, and Browser 2_33.

In the embodiment of FIG. 10A, one smart viewer application controls all browsers across first computer monitor 1000 and second computer monitor 1002. And this is only exemplary, more monitors can be included. Smart viewer application allows for synchronization, coordination, and communication between browsers, even across multiple physical monitors or screens. While a user may be scrolling, rotating, or controlling certain views of a browser, for an example, multiple browsers can synchronize the angle of scrolling, angle of view, or control in place, respectively. The communication between browsers to enable synchronization and coordination will be discussed further with reference to FIG. 10B.

Figure 10B:
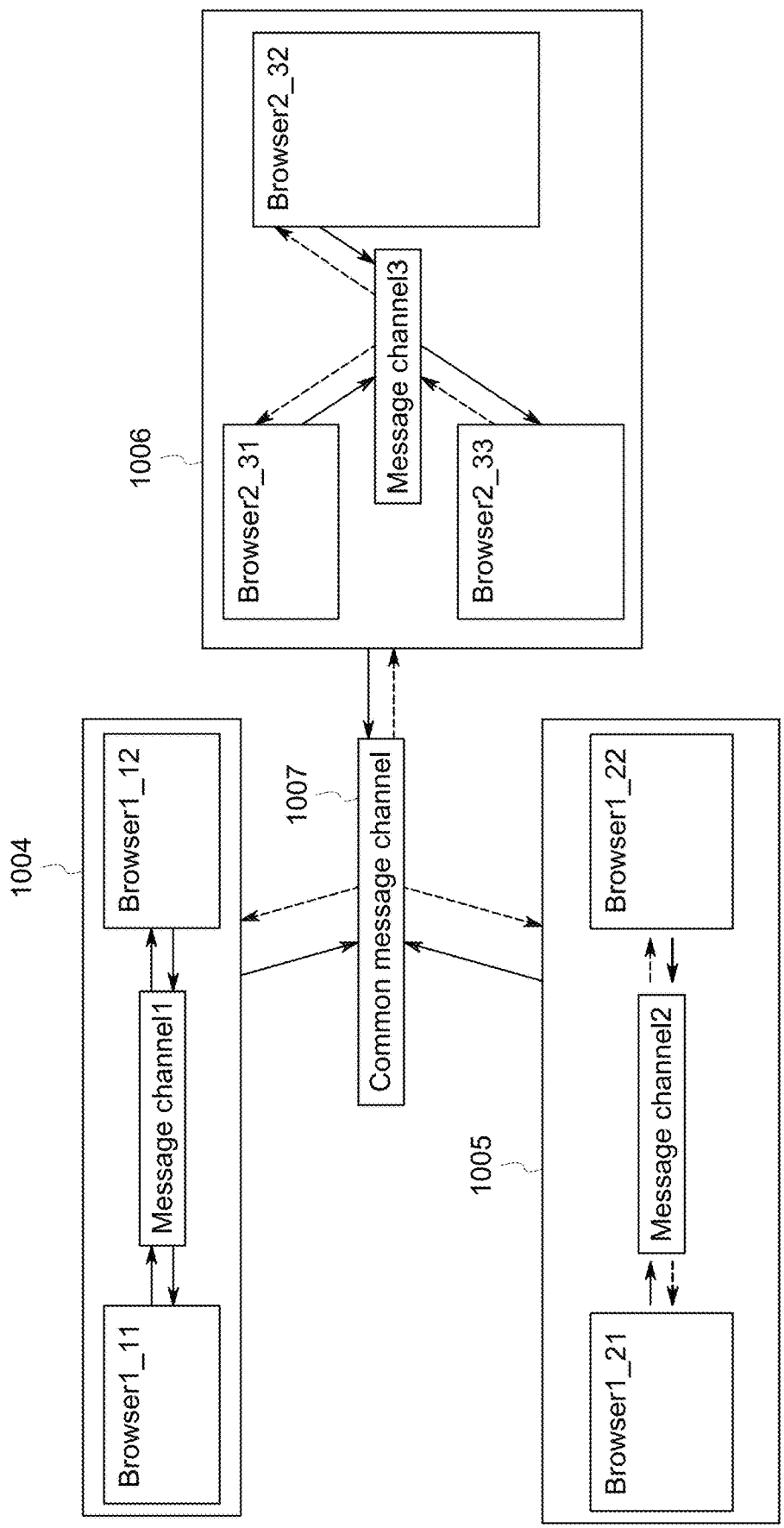
FIG. 10B shows cross browser communication in a multi-browser system, according to an embodiment.

FIG. 10B shows cross browser communication in a multi-browser system, according to an embodiment. FIG. 10B includes cross browser communication block 1004, 1005, 1006 and common message channel 1007. Cross browser communication block 1004 includes Browser 1_11, Message channel 1, and Browser 1_12. Cross browser communication block 1005 includes Browser 1_21, Message channel 2, and Browser 1_22. Communication browser block 1006 includes Browser 2_31, Message channel 3, Browser 2_32, and Browser 2_33.

In this embodiment, each browser group (shown as cross browser communication blocks) can communicate using a dedicated messaging interface, such as Message channel 1. Here the communication between browsers is on the local device. Message channel 1 allows for coordination, communication, and synchronization between Browser 1_11 and Browser 1_12. Message channels can be done in many messaging schemes, such as application programming interface (API), broadcast channel API, or a service worker API. A service worker API can be single thread which is running apart from all the browser and all the browsers run as a client for Service worker API thread. On service worker thread can be used to monitor all the threads and can limit the fetching of same data from the server. For example, if there is same query from the different browsers service worker API can limit all the request to one request and can serve other browser from the one response to all. These are local to the client/local computer, and are not over external networking such as the internet. Further, the system can use the APIs to monitor the health of all the browsers from one service worker thread. Common message channel 1007 can provide communications between browsers individually or between cross browser communication blocks.

Figure 11:
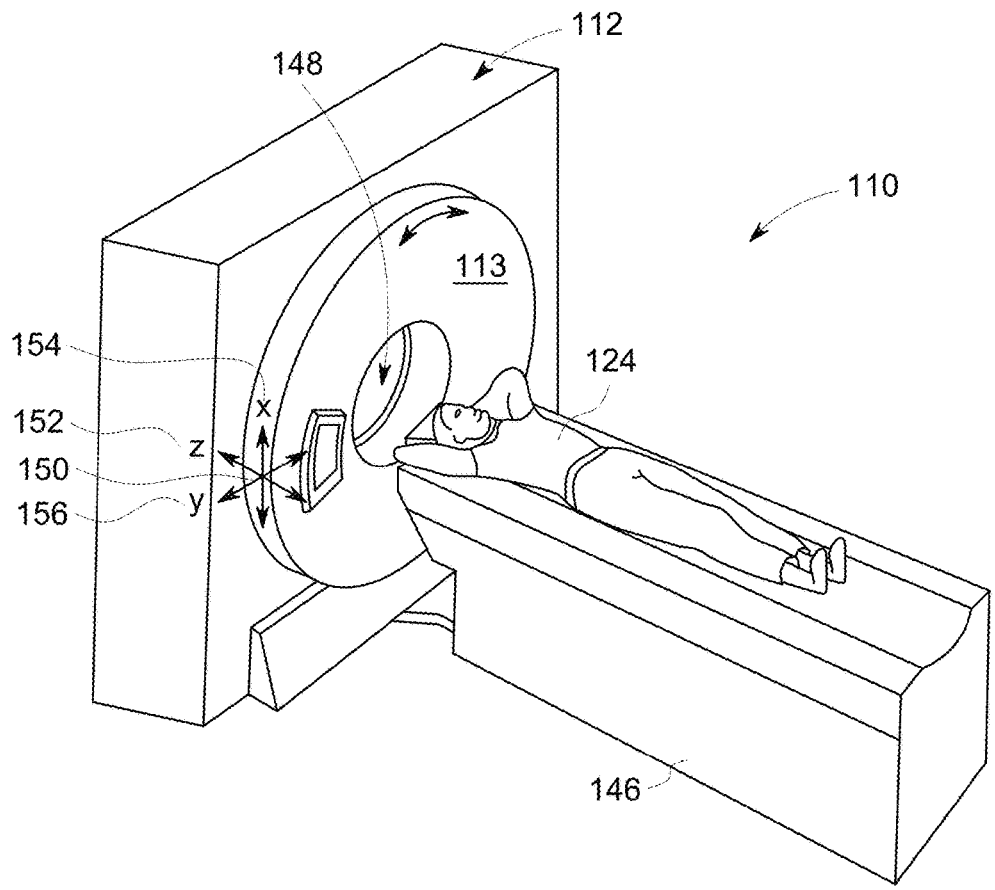
FIG. 11 shows a medical imaging system for providing medical image data, according to an embodiment.
Figure 12:
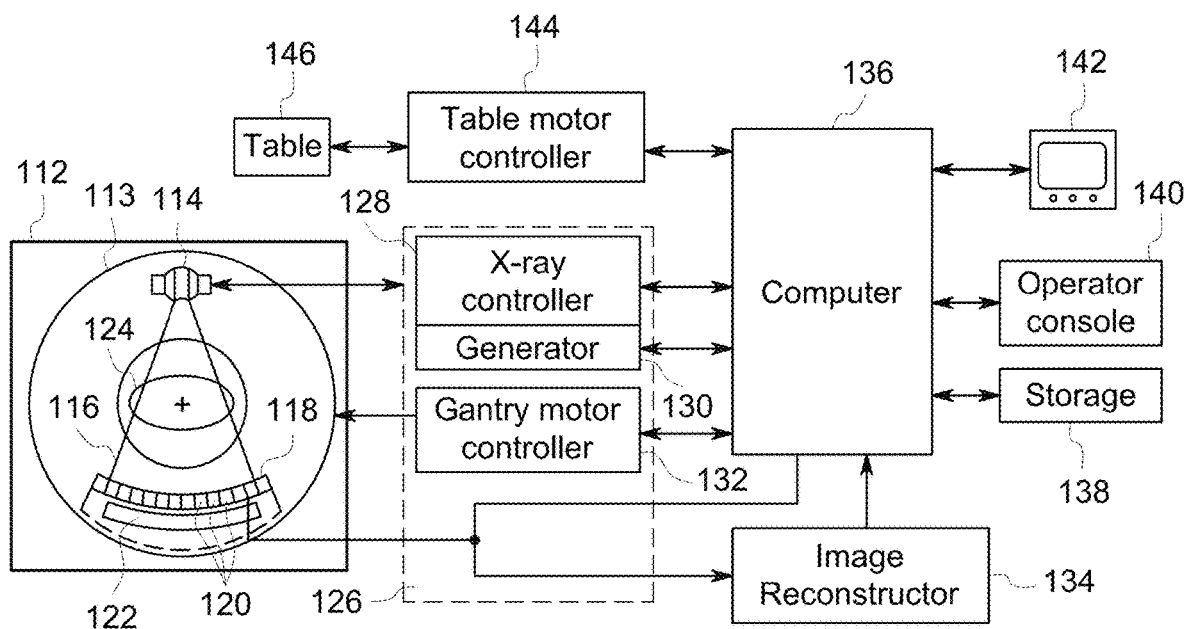
FIG. 12 shows a block schematic diagram of a medical imaging and multi-browser system, according to an embodiment.

FIG. 11 shows a medical imaging system for providing medical image data, according to an embodiment. FIG. 12 shows a block schematic diagram of a medical imaging and multi-browser system, according to an embodiment. These are an exemplary imaging modality that generates the medical images that are viewed on operated on display 142 as computer 136 may be running the smart viewer software disclosed herein.

FIGS. 11 and 12 show a computed tomography (CT) imaging system 110 including a gantry 112. Gantry 112 has a rotary member 113 an x-ray source 114 that projects a beam of x-rays 116 toward a detector assembly 118 on the opposite side of the rotary member 113. A main bearing may be utilized to attach the rotary member 113 to the stationary structure of the gantry 112. X-ray source 114 includes either a stationary target or a rotating target. Detector assembly 118 is formed by a plurality of detectors 120 and data acquisition systems (DAS) 122, and can include a collimator. The plurality of detectors 120 sense the projected x-rays that pass through a subject 124, and DAS 122 converts the data to digital signals for subsequent processing. Each detector 120 produces an analog or digital electrical signal that represents the intensity of an impinging x-ray beam and hence the attenuated beam as it passes through subject 124. During a scan to acquire x-ray projection data, rotary member 113 and the components mounted thereon can rotate about a center of rotation.

Rotation of rotary member 113 and the operation of x-ray source 114 are governed by a control mechanism 126 of CT system 110. Control mechanism 126 can include an x-ray controller 128 and generator 130 that provide power and timing signals to x-ray source 114 and a gantry motor controller 132 that controls the rotational speed and position of rotary member 113. An image reconstructor 134 receives sampled and digitized x-ray data from DAS 122 and performs high speed image reconstruction. The reconstructed image is output to a computer 136 which stores the image in a computer storage device 138.

Computer 136 also receives commands and scanning parameters from an operator via operator console 140 that has some form of operator interface, such as a keyboard, mouse, touch sensitive controller, voice activated controller, or any other suitable input apparatus. Display 142 allows the operator to observe the reconstructed image and other data from computer 136. The operator supplied commands and parameters are used by computer 136 to provide control signals and information to DAS 122, x-ray controller 128, and gantry motor controller 132. In addition, computer 136 operates a table motor controller 144 which controls a motorized table 146 to position subject 124 and gantry 112. Particularly, table 146 moves a subject 124 through a gantry opening 148, or bore, in whole or in part. A coordinate system 150 defines a patient or Z-axis 152 along which subject 124 is moved in and out of opening 148, a gantry circumferential or X-axis 154 along which detector assembly 118 passes, and a Y-axis 156 that passes along a direction from a focal spot of x-ray tube 114 to detector assembly 118.

A user may operate operator console 140 to interact with and view medical information, including medical images taken by CT system 110. Computer 136 may have a CPU, memory, and storage 138 that allow for processes to run in them. Computer 136 can have smart viewer software which allows for multi-browser systems as described herein, thus enabling coordinated viewing of medical images while managing memory and CPU usage well.

Figure 13:
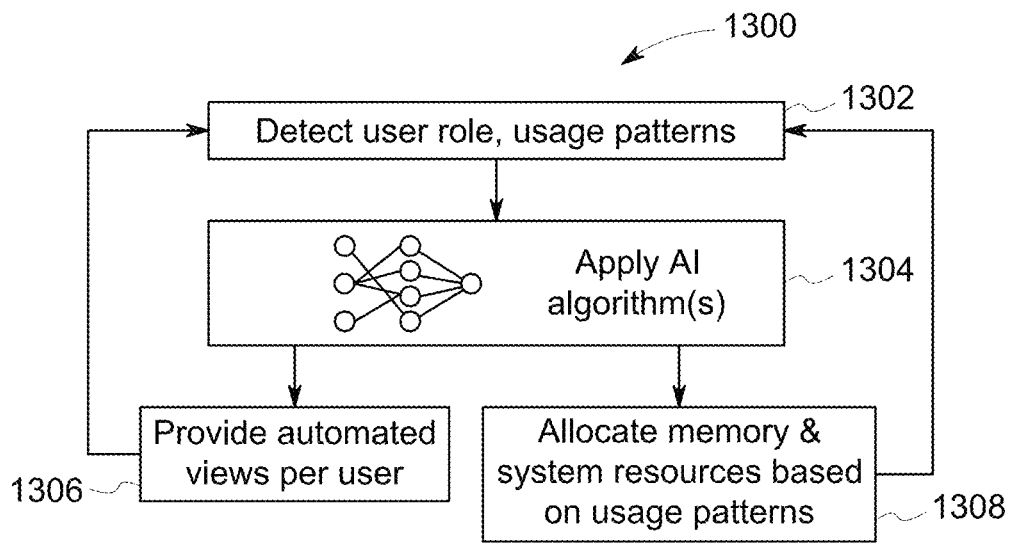
FIG. 13 shows a process for providing a multi-browser viewing system, according to an embodiment.

FIG. 13 shows a process for providing a multi-browser viewing system, according to an embodiment. Learning process 1300 allows the smart multi-browser viewing system to learn and automatically improve how it both provides browser viewing to the user and handles computer resources efficiently.

In step 1302, the system detects aspects of the situation. This may be the user's role, the user's usage patterns, patterns of other users with related medical conditions, past decisions made with similar information, which browsers are generally placed on which parts of the screen by users for best viewing, best rated views of information or most viewed angles of image viewing based on body part, and the like. The more data the system monitors and notes, the more that can be used as input data in learning process 1300.

In step 1304, the system applies one or more artificial intelligence algorithms to provide for system learning based on the input data from step 1302. This artificial intelligence may be neural network based, deep learning based, machine learning based, or other technologies for learning and improving computer algorithms and applications. The AI algorithms can be both related to displaying of data and computer process management.

In step 1306, the system provides automated views. This may be per user or based on other factors. The system provides an improved viewer experience based on the results of AI learning in step 1304. This provides a better experience for the user that is more tailored to the medical conditions or situations that the multi-browser system is handling. For example, if one radiologist always has the EMR as one browser window and another radiologist never has the EMR as a browser window, then the system can learn this about those users and provide the EMR data each time to the first radiologist but not always provide for the second radiologist. The more the system can provide smarter user interfaces, the faster and better decisions can be made in healthcare, saving lives of patients and improving the jobs of the healthcare worker.

In step 1308, the system allocates memory and system resources. This may be based on usage patterns. The system can manage processes with memory resources better as it learns how the users interact with the system. For example, if there is a certain type of image data loaded into certain browsers that are viewed the most, that process can receive priority access to the CPU and fastest memory access.

Figure 14:
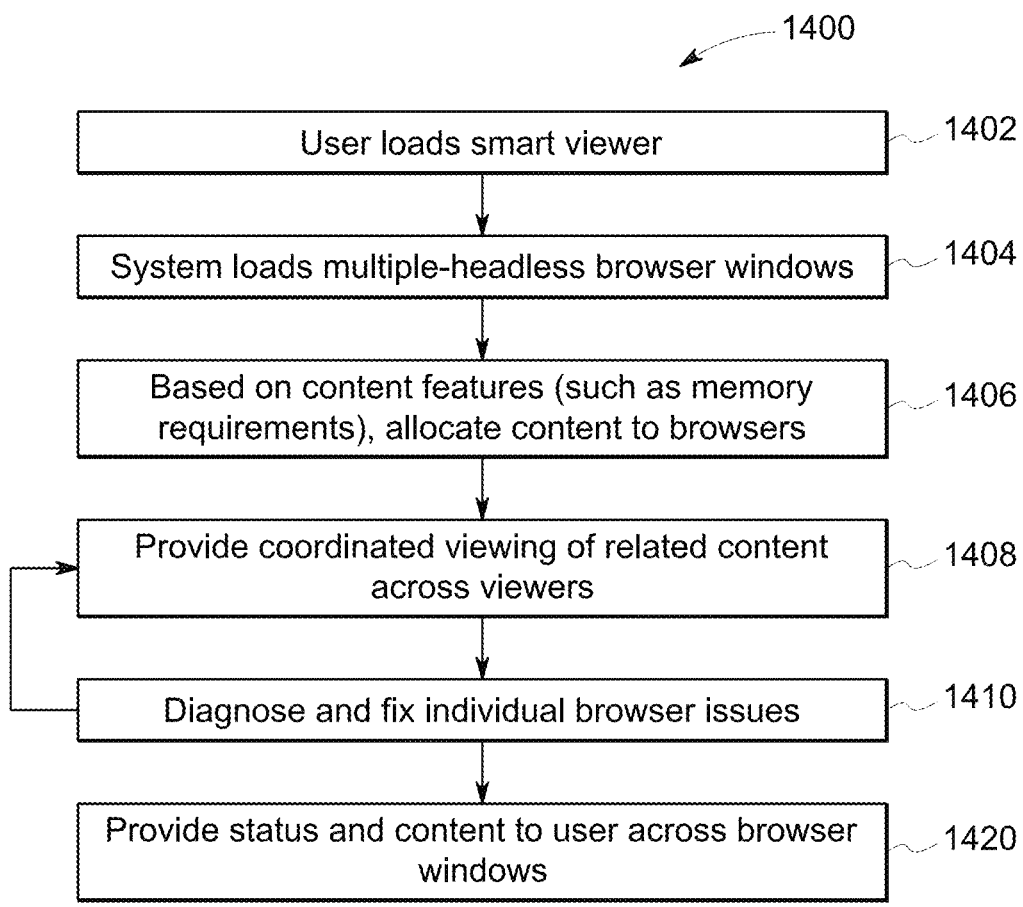
FIG. 14 shows a process for coordinated viewing in a multi-browser system, according to an embodiment.

FIG. 14 shows a process 1400 for coordinated viewing in a multi-browser system, according to an embodiment. In step 1402, the user loads the smart viewer on their system, initiating a multi-browser user experience. In step 1404, the smart viewer system loads multiple headless browser windows.

In step 1406, the system allocates content to the browsers. Each browser window has some content in for viewing and/or interacting with. In a medical example the content may be as shown in FIG. 2 and FIG. 3, for example. This allocation considers memory requirements and processor load, as discussed in connection with FIG. 9 and throughout. For example, only five images may be loaded into one browser if they are very large, whereas 50 may be loaded into another browser if they are smaller in size. Or if a video would use a large amount of processing power to display based on its size or video codec, it may be put in its own browser instead of putting it with other videos sharing a browser.

In step 1408, the system provides coordinated viewing of related content across viewers. This may include having a controller browser for a user to select how the coordinating viewing will work. The coordinated viewing between browsers is accomplished through message channels between browsers. The coordinated viewing helps users quickly see connections across various content in different browsers. This is discussed further in connection with FIG. 4, FIG. 10A, and FIG. 10B.

In step 1410, the system can diagnose and fix issues related to individual browsers. Individual browsers may have computer health issues with memory, processing, and other issues. Because each browser is its own computer process, these issues do not cause other browsers to slow down or fail. The system can detect these issues and automatically fix them and/or propose specific actions in the user interface for the users to fix the issue. This is discussed further in connection with FIG. 7A and FIG. 7B.

In step 1420, the system provides browser status and content to the user across browser windows. Both content requested and browser status may be provided. And the user can interact with the system to have a positive, fast, and helpful multi-browser user experience.

The benefits of systems and methods herein are both technical and practical. The performance improvement on the computer technology helps the system avoid hang ups and processes crashes. The CPU and memory of the system can be used optimally. The user's productivity increases. Automatic correction of browser issues helps non-experienced users quickly fix issues and get back to focusing on the content. And the system can run cine with larger number of images and videos. Smooth cine running is a very desired benefit in the medical community.

The systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which may be explicitly illustrated in this disclosure.

The illustrated aspects of the disclosure may also be practiced in distributed computing environments where certain tasks are performed by remote processing devices that are linked through a communications network. In a distributed computing environment, program modules can be located in both local and remote memory storage devices.

Moreover, it is to be appreciated that various components described in this description can include electrical circuit(s) that can include components and circuitry elements of suitable value in order to implement the embodiments of the subject innovation(s). Furthermore, it can be appreciated that many of the various components can be implemented on one or more integrated circuit (IC) chips. For example, in one embodiment, a set of components can be implemented in a single IC chip. In other embodiments, one or more of respective components are fabricated or implemented on separate IC chips.

Figure 15:
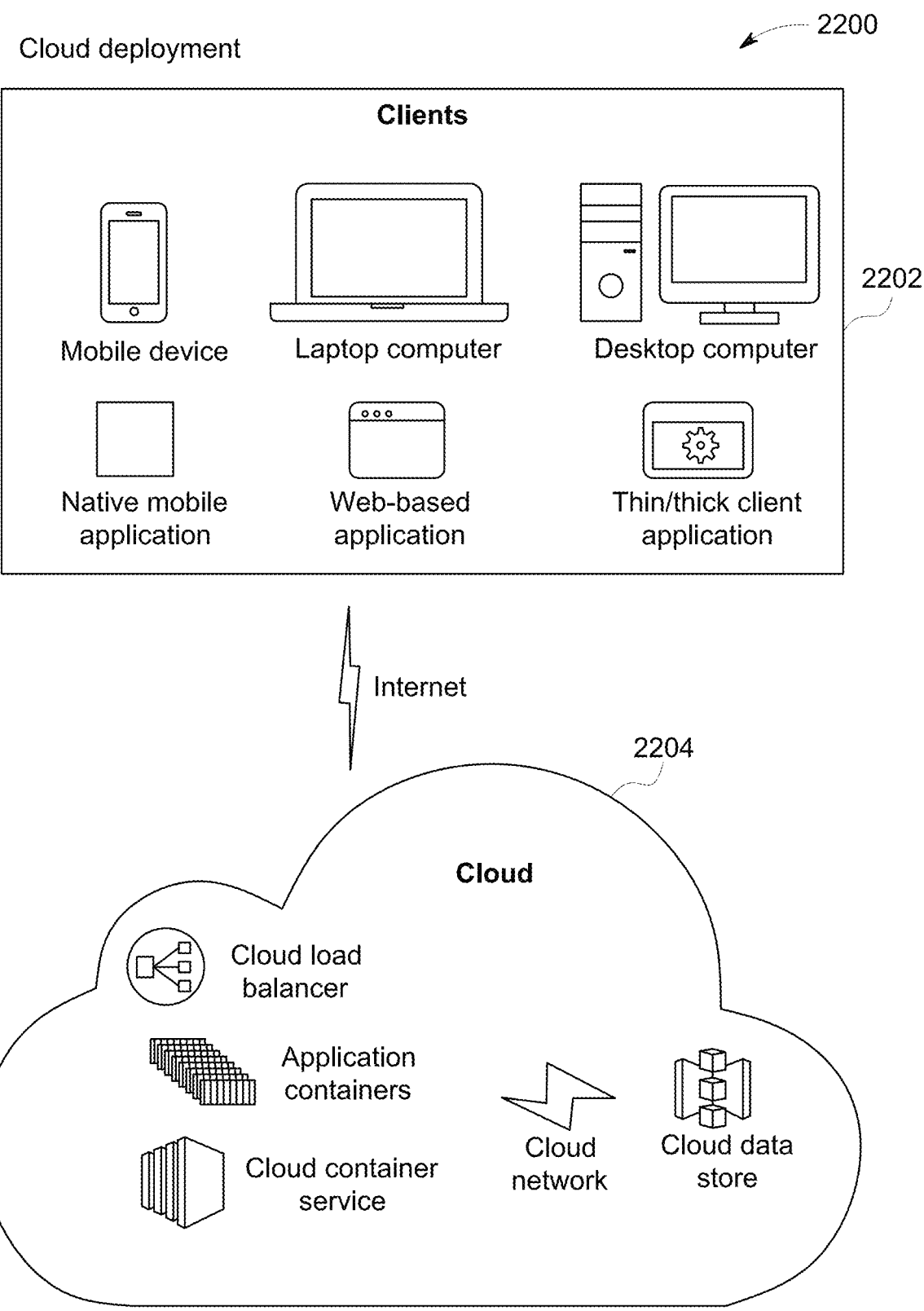
FIG. 15 shows a schematic block diagram of a sample-computing environment, according to an embodiment.

FIG. 15 illustrates a schematic block diagram of an example computing environment 2200 in accordance with this disclosure in which the subject systems, methods and computer readable media can be deployed. The computing environment 2200 includes a cloud deployment architecture consisting of one or more clients 2202 (e.g., laptops, smart phones, PDAs, media players, computers, portable electronic devices, tablets, and the like) that can be communicatively coupled to a system cloud 2204 via a network (e.g., the Internet). The system cloud 2204 can include a cloud load balances, one or more application container, one or more cloud service containers, a cloud data store, and a cloud network that communicatively couples the one or more cloud components to the cloud data store. In accordance with the cloud deployment architecture, the clients 2202 can include one or more clients devices (e.g., a mobile device, a laptop computer, a desktop computer, etc.) which can include or employ a suitable application (e.g., a native mobile application, a web-based application, a thin/thick client application, etc.) to access and employ one or more features and functionalities of the subject native/reconstructed medical imaging systems deployed in the system cloud 2204. In various implementations, the one or more components of system 100 can be distributed between the clients 2202 and the system cloud 2204.

Figure 16:
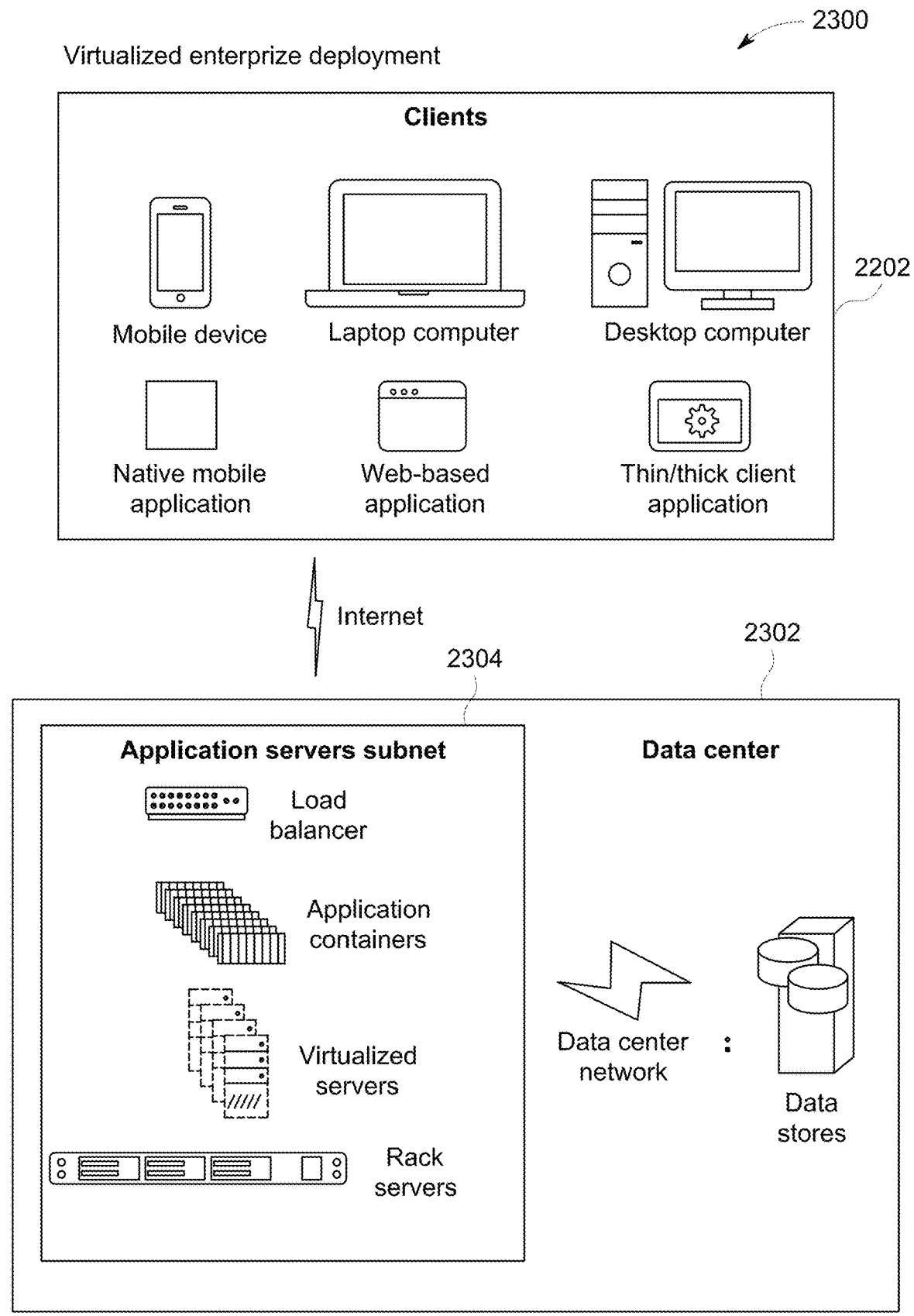
FIG. 16 shows a schematic block diagram of another sample-computing environment, according to an embodiment.

FIG. 16 illustrates a schematic block diagram of another example computing environment 2300 in accordance with this disclosure in which the subject systems (e.g., systems 100 and the like), methods and computer readable media can be deployed. The computing environment 2300 includes a virtualized enterprise deployment consisting of one or more clients 2202 that can be communicatively coupled to a remote data center 2302 via a network (e.g., the Internet). The remote data center 2302 can include an application servers subnet 2304 which can provide a load balancer, one or more application containers, one or more virtualized servers and one or more rack servers. The data center 2302 can also include one or more data stores that can be communicatively coupled to the application servers subnet 2304 via a data center network. In accordance with the virtualized enterprise deployment, the clients 2202 can include one or more clients devices (e.g., a mobile device, a laptop computer, a desktop computer, etc.) which can include or employ a suitable application (e.g., a native mobile application, a web-based application, a thin/thick client application, etc.) to access and employ one or more features and functionalities of the subject native/reconstructed medical imaging systems deployed in the data center 2302 and application servers subnet 2304. In various implementations, the one or more components of systems 100 can be distributed between the clients 2202 and the application servers subnet 2304 and the one or more data stores can be provided remotely at the data center 2302.

Figure 17:
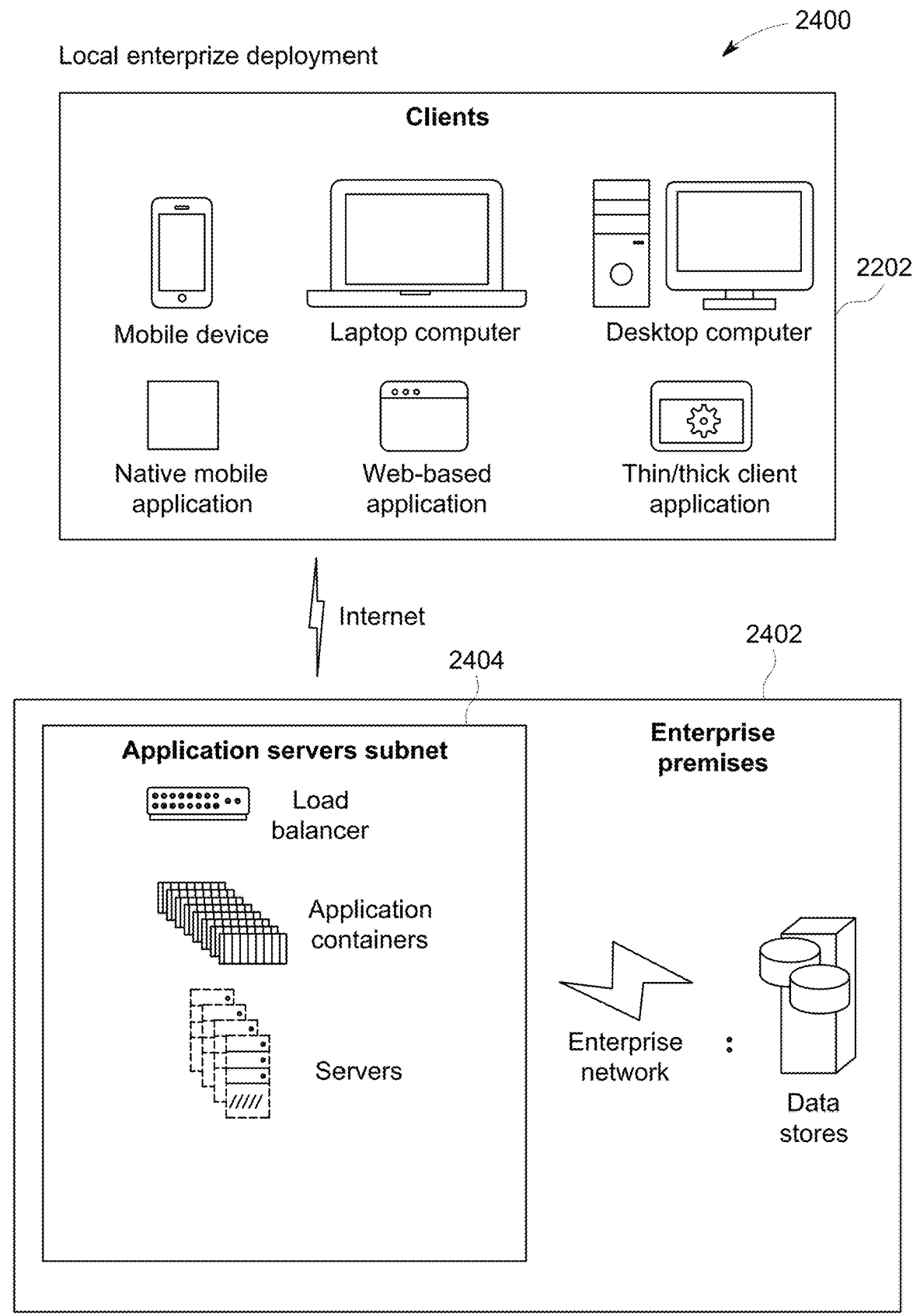
FIG. 17 shows a schematic block diagram of another sample-computing environment, according to an embodiment.

FIG. 17 illustrates a schematic block diagram of another example computing environment 2400 in accordance with this disclosure in which the subject systems, methods and computer readable media can be deployed. The computing environment 2400 includes a local enterprise deployment consisting of one or more clients 2202 that can be communicatively coupled to an application servers subnet 2404 via a network (e.g., the Internet). In accordance with this embodiment, the application servers subnet 2404 can be provided at the enterprise premises 2402 (e.g., as opposed to a remote data center 2302). The application servers subnet 2404 can include a load balancer, one or more application containers and one or more servers. The application servers subnet 2404 can be communicatively coupled to one or more data stores provided at the enterprise premises 2402 via an enterprise network. Similar to the cloud and virtualized enterprise deployments, the clients 2202 can include one or more clients devices (e.g., a mobile device, a laptop computer, a desktop computer, etc.) which can include or employ a suitable application (e.g., a native mobile application, a web-based application, a thin/thick client application, etc.) to access and employ one or more features and functionalities of the subject native/reconstructed medical imaging systems (e.g., system 100 and the like) deployed at the enterprise premises 2402 and the application servers subnet 2404. In various implementations, the one or more components of systems herein can be distributed between the clients 2202 and the application servers subnet 2404 and the one or more data stores can be provided at the enterprise premises 2402.

Figure 18:
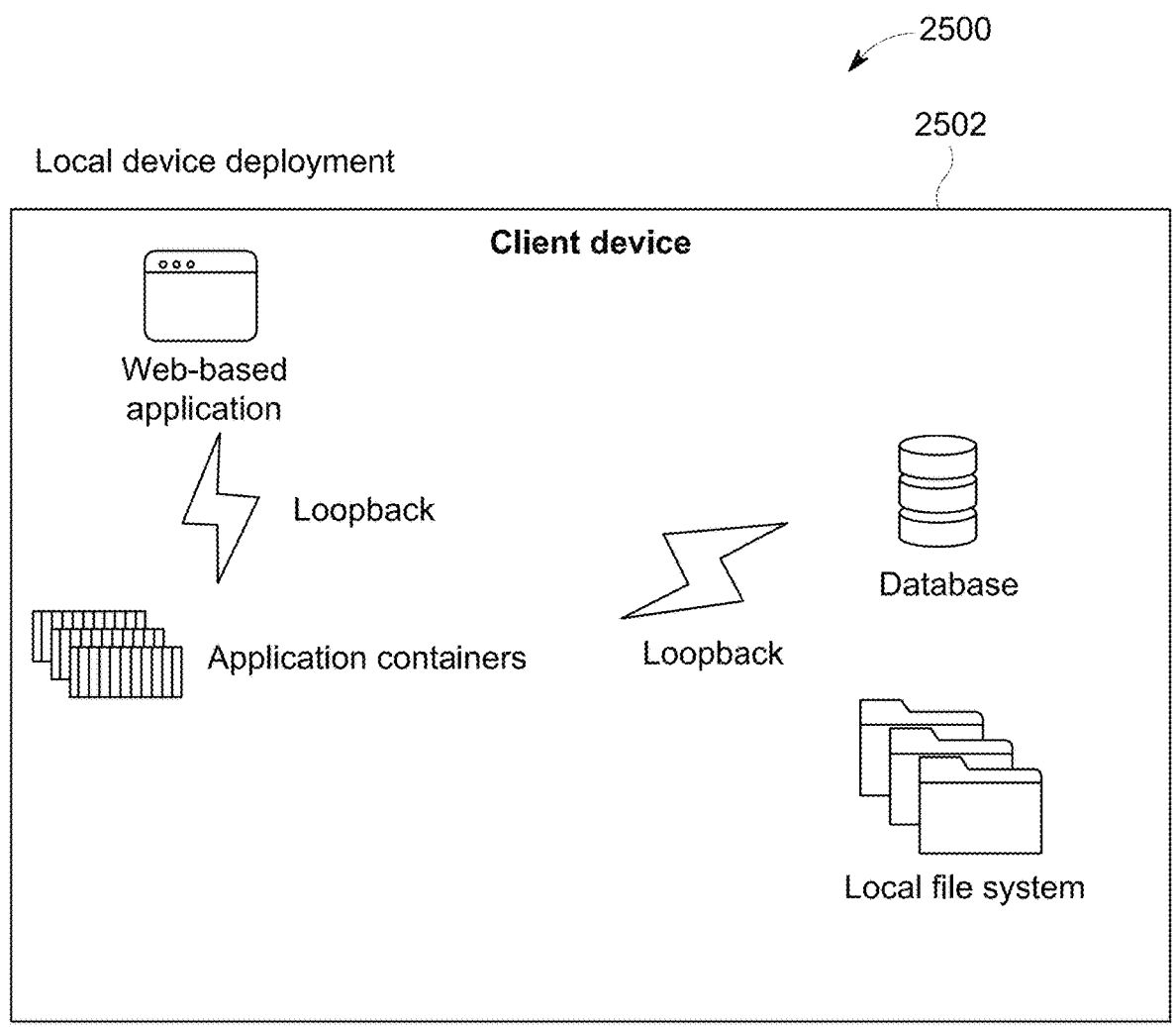
FIG. 18 shows a schematic block diagram of another sample-computing environment, according to an embodiment.

FIG. 18 illustrates a schematic block diagram of another example computing environment in accordance with this disclosure in which the subject systems, methods and computer readable media can be deployed. The computing environment includes a local device deployment in which all of the components of systems herein are provided at a single client device 2502. With this implementation, the client device 2502 can include a web-based application which can be communicatively coupled via a loopback to one or more application containers. The one or more application containers can be communicatively coupled via a loopback to one or more databases and/or one or more local file systems.

Figure 19:
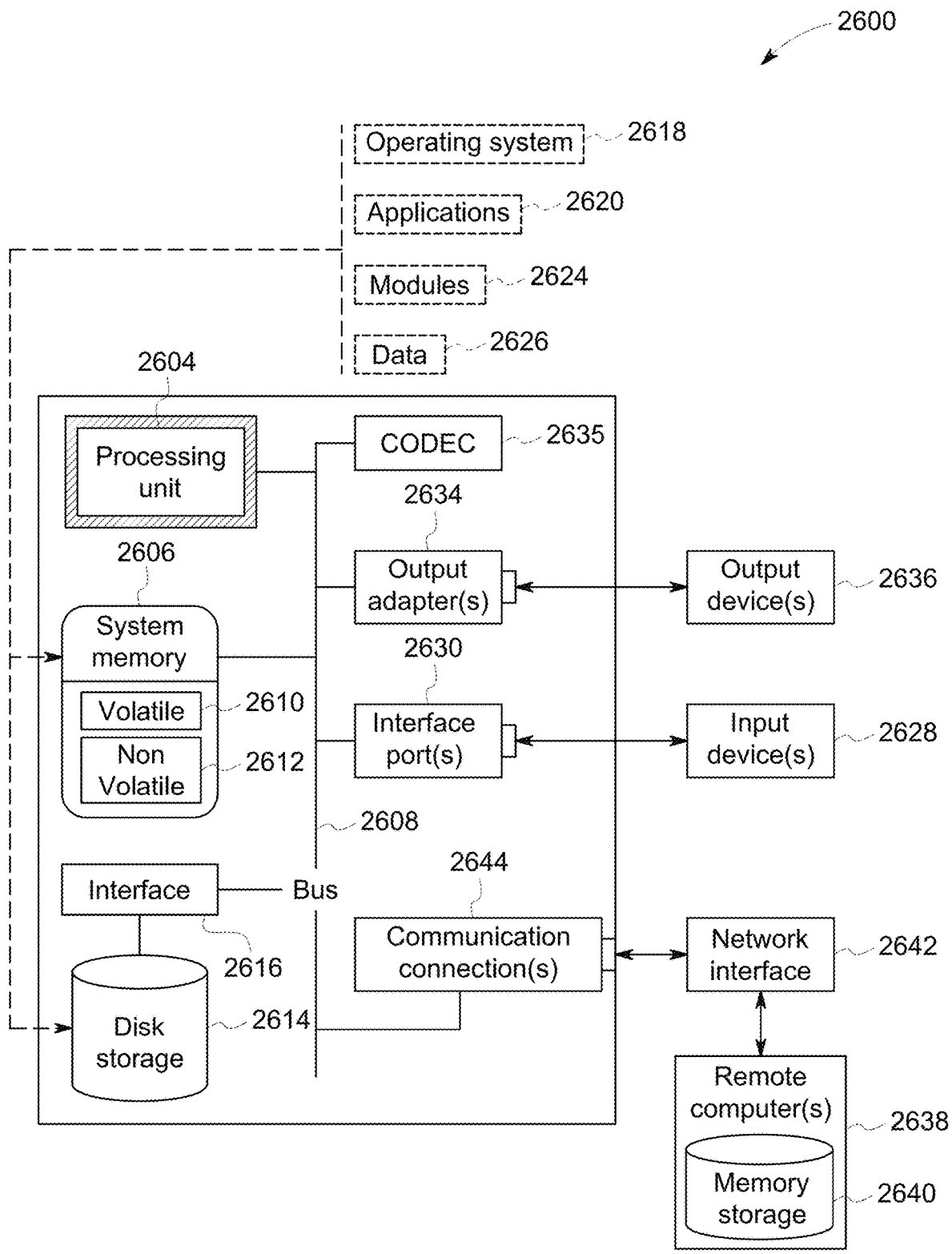
FIG. 19 shows a schematic block diagram illustrating a suitable operating environment, according to an embodiment.

With reference to FIG. 19, a suitable environment 2600 for implementing various aspects of the claimed subject matter includes a computer 2602. The computer 2602 includes a processing unit 2604, a system memory 2606, a codec 2605, and a system bus 2608. The system bus 2608 couples system components including, but not limited to, the system memory 2606 to the processing unit 2604. The processing unit 2604 can be any of various available processors. Dual microprocessors and other multiprocessor architectures also can be employed as the processing unit 2604.

The system bus 2608 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 22104), and Small Computer Systems Interface (SCSI).

The system memory 2606 includes volatile memory 2610 and non-volatile memory 2612. The basic input/output system (BIOS), containing the basic routines to transfer information between elements within the computer 2602, such as during start-up, is stored in non-volatile memory 2612. In addition, according to present innovations, codec 2605 may include at least one of an encoder or decoder, wherein the at least one of an encoder or decoder may consist of hardware, a combination of hardware and software, or software. Although, codec 2605 is depicted as a separate component, codec 2605 may be contained within non-volatile memory 2612. By way of illustration, and not limitation, non-volatile memory 2612 can include read only memory (ROM), programmable ROM (PROM), electrically programmable ROM (EPROM), electrically erasable programmable ROM (EEPROM), or flash memory. Volatile memory 2210 includes random access memory (RAM), which acts as external cache memory. According to present aspects, the volatile memory may store the write operation retry logic and the like. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM).

Computer 2602 may also include removable/non-removable, volatile/non-volatile computer storage medium. FIG. 19 illustrates, for example, disk storage 2614. Disk storage 2614 includes, but is not limited to, devices like a magnetic disk drive, solid state disk (SSD) floppy disk drive, tape drive, Zip drive, flash memory card, or memory stick. In addition, disk storage 2614 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 2614 to the system bus 2608, a removable or non-removable interface is typically used, such as interface 2616.

It is to be appreciated that FIG. 16 describes software that acts as an intermediary between users and the basic computer resources described in the suitable operating environment 2600. Such software includes an operating system 2618. Operating system 2618, which can be stored on disk storage 2614, acts to control and allocate resources of the computer system 2602. Applications 2620 take advantage of the management of resources by operating system 2618 through program modules 2624, and program data 2626, such as the boot/shutdown transaction table and the like, stored either in system memory 2606 or on disk storage 2614. It is to be appreciated that the claimed subject matter can be implemented with various operating systems or combinations of operating systems.

A user enters commands or information into the computer 2602 through input device(s) 2628. Input devices 2628 include, but are not limited to, a pointing device such as a mouse, trackball, stylus, touch pad, keyboard, microphone, joystick, game pad, satellite dish, scanner, TV tuner card, digital camera, digital video camera, web camera, microphone, and the like. These and other input devices connect to the processing unit 2604 through the system bus 2608 via interface port(s) 2630. Interface port(s) 2630 include, for example, a serial port, a parallel port, a game port, and a universal serial bus (USB). Output device(s) 2636 use some of the same type of ports as input device(s). Thus, for example, a USB port may be used to provide input to computer 2602, and to output information from computer 2602 to an output device 2636. Output adapter 2634 is provided to illustrate that there are some output devices 2636 like monitors, speakers, and printers, among other output devices 2636, which require special adapters. The output adapters 2634 include, by way of illustration and not limitation, video and sound cards that provide a means of connection between the output device 2636 and the system bus 2608. It should be noted that other devices and/or systems of devices provide both input and output capabilities such as remote computer(s) 2638.

Computer 2602 can operate in a networked environment using logical connections to one or more remote computers, such as remote computer(s) 2638. The remote computer(s) 2638 can be a personal computer, a server, a router, a network PC, a workstation, a microprocessor based appliance, a peer device, a smart phone, a tablet, or other network node, and typically includes many of the elements described relative to computer 2602. For purposes of brevity, only a memory storage device 2640 is illustrated with remote computer(s) 2638. Remote computer(s) 2638 is logically connected to computer 2602 through a network interface 2642 and then connected via communication connection(s) 2644. Network interface 2642 encompasses wire and/or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 2644 refers to the hardware/software employed to connect the network interface 2642 to the bus 2608. While communication connection 2644 is shown for illustrative clarity inside computer 2602, it can also be external to computer 2602. The hardware/software necessary for connection to the network interface 2642 includes, for exemplary purposes only, internal and external technologies such as, modems including regular telephone grade modems, cable modems and DSL modems, ISDN adapters, and wired and wireless Ethernet cards, hubs, and routers.

What has been described above includes examples of the embodiments of the present invention. It is, of course, not possible to describe every conceivable combination of components or methodologies for purposes of describing the claimed subject matter, but it is to be appreciated that many further combinations and permutations of the subject innovation are possible. Accordingly, the claimed subject matter is intended to embrace all such alterations, modifications, and variations that fall within the spirit and scope of the appended claims. Moreover, the above description of illustrated embodiments of the subject disclosure, including what is described in the Abstract, is not intended to be exhaustive or to limit the disclosed embodiments to the precise forms disclosed. While specific embodiments and examples are described in this disclosure for illustrative purposes, various modifications are possible that are considered within the scope of such embodiments and examples, as those skilled in the relevant art can recognize.

In particular and in regard to the various functions performed by the above described components, devices, circuits, systems and the like, the terms used to describe such components are intended to correspond, unless otherwise indicated, to any component which performs the specified function of the described component (e.g., a functional equivalent), even though not structurally equivalent to the disclosed structure, which performs the function in the disclosure illustrated exemplary aspects of the claimed subject matter. In this regard, it will also be recognized that the innovation includes a system as well as a computer-readable storage medium having computer-executable instructions for performing the acts and/or events of the various methods of the claimed subject matter.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

As used in this application, the terms "component," "system," or the like are generally intended to refer to a computer-related entity, either hardware (e.g., a circuit), a combination of hardware and software, software, or an entity related to an operational machine with one or more specific functionalities. For example, a component may be, but is not limited to being, a process running on a processor (e.g., digital signal processor), a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. Further, a "device" can come in the form of specially designed hardware; generalized hardware made specialized by the execution of software thereon that enables the hardware to perform specific function; software stored on a computer readable storage medium; software transmitted on a computer readable transmission medium; or a combination thereof.

Moreover, the words "example" or "exemplary" are used in this disclosure to mean serving as an example, instance, or illustration. Any aspect or design described in this disclosure as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Computing devices typically include a variety of media, which can include computer-readable storage media and/or communications media, in which these two terms are used in this description differently from one another as follows. Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

In view of the exemplary systems described above, methodologies that may be implemented in accordance with the described subject matter will be better appreciated with reference to the flowcharts of the various figures. For simplicity of explanation, the methodologies are depicted and described as a series of acts. However, acts in accordance with this disclosure can occur in various orders and/or concurrently, and with other acts not presented and described in this disclosure. Furthermore, not all illustrated acts may be required to implement the methodologies in accordance with certain aspects of this disclosure. In addition, those skilled in the art will understand and appreciate that the methodologies could alternatively be represented as a series of interrelated states via a state diagram or events. Additionally, it should be appreciated that the methodologies disclosed in this disclosure are capable of being stored on an article of manufacture to facilitate transporting and transferring such methodologies to computing devices. The term article of manufacture, as used in this disclosure, is intended to encompass a computer program accessible from any computer-readable device or storage media It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A system, comprising:
a processor for executing a plurality of computer browser processes;
a memory that stores digital content for use by said computer browser processes during execution by the processor;
a monitor for displaying a user interface;
a first browser process executed by the processor that accesses digital content from the memory, wherein the first browser process displays digital content in a user interface window on the monitor;
a second browser process executed by the processor that accesses digital content from the memory, wherein the second browser process displays digital content in a user interface window on the monitor simultaneously to the first browser process;
wherein each browser process has a separate allocation of memory that is based on a size of the digital content to be displayed by that browser process; and
wherein the user interface windows for each browser process are displayed in a hanging layout on the monitor, and wherein the first browser process and the second browser process display different sequences of cinematographic medical images, wherein one or more of the cinematographic medical images are pre-loaded into the allocation of memory for the first browser process and the allocation of memory for the second browser process prior to displaying the digital content in the user interface windows.

2. The system of claim 1, further comprising:
an input device for a user to interact with the user interface;
a coordination browser process executed by the processor that provides coordination between the first browser process and second browser process; and
wherein the coordination browser process allows the input device to manipulate digital content simultaneously in both the first browser process and second browser process.

3. The system of claim 2, wherein:
the digital content displayed in both the first browser process and second browser process is medical digital content;
the medical digital content displayed in both the first browser process and the second browser process is not the same digital content; and
the medical digital content in both the first browser process and the second browser process are related to the same patient.

4. The system of claim 2, wherein:
the coordination browser process uses at least one message channel process to facilitate cross-browser coordination.

5. The system of claim 2, wherein:
the digital content manipulated is a cine.

6. The system of claim 1, further comprising:
a second monitor for displaying the user interface;
a third browser process executed by the processor that accesses digital content from the memory, wherein the third browser process displays digital content in a user interface window on the second monitor;
a common message channel for cross browser communication between at least two of the browser processes; and
wherein at least two of the browser processes coordinate their displayed digital content through the common message channel.

7. The system of claim 6, wherein:
the common message channel is implemented as an application programming interface (API).

8. The system of claim 1, wherein:
the first browser process and the second browser process are displayed on the monitor in headless user interface windows.

9. The system of claim 1, further comprising:
a controller browser process executed by the processor that allows a user to access control functions related to at least one of browser processes, wherein the controller browser process displays control functions in a user interface window on the monitor; and each control function allows a user to interact with the digital content in at least one of the first browser process or the second browser process.

10. The system of claim 1, wherein:
the first browser process and second browser process detect a digital health of its respective process, and provide an indication on the user interface related to the digital health of its process.

11. The system of claim 10, wherein:
the user interface can accept a user command to restart at least one of the first browser process or second browser process.

12. The system of claim 10, wherein:
the digital health of a computer process is related to its interaction with the memory.

13. The system of claim 1, wherein:
each of the first browser process and second browser process can detect its respective digital health, related to its interactions with the processor and memory; and
if the digital health is detected as not healthy, each browser process can restart itself.

14. The system of claim 1, wherein:
as the processor allocates digital content to each browser process, the size of the digital content is considered compared to the separate allocation of memory for the related browser process.

15. The system of claim 1, wherein:
the processor executes the steps of:
detecting the user interface usage patterns of at least one user; and
running an artificial intelligence algorithm based on the usage patterns to either (a) provide automated user interface windows to the user or (b) allocate memory and system resources.

16. A computer-implemented method, comprising the steps of:
displaying a user interface on a monitor;
loading multiple browser windows with digital content, wherein each browser window is run as a separate computer browser process and has a separate memory allocation than the other browser windows, and wherein the memory allocation for each browser window is based on a size of the digital content to be displayed by that browser window;
displaying the multiple browser windows within the user interface, wherein the multiple browser windows are displayed in a hanging layout on the monitor;
providing coordination between the multiple browser windows through digital communication channels; and
allowing for user interaction with the multiple browser windows, and wherein a first browser process and a second browser process display different sequences of cinematographic medical images, wherein one or more of the cinematographic medical images are pre-loaded into the memory allocation for the first browser process and the memory allocation for the second browser process prior to displaying the digital content in the user interface.

17. The computer implemented method of claim 16, wherein:
the digital content displayed in both a first browser window and a second browser window is medical digital content;
the medical digital content displayed in both the first browser window and the second browser window is not the same; and
the medical digital content in both browser windows is related to the same patient.

18. The computer implemented method of claim 16, wherein:
each browser window detects a digital health of its respective computer browser process and provides an indication on the user interface related to the digital health of its respective computer browser process.

19. The computer implemented method of claim 16, wherein:
each browser window can detect its digital health, related to its interactions with the processor and memory; and
if its digital health is not healthy, the browser window can restart its computer browser process.

\* \* \* \* \*